(12) United States Patent (10) Patent No.: US 8,574,904 B2
Tsuji et al. (45) Date of Patent: Nov. 5, 2013

(54) METHOD FOR PRODUCTION OF MESENCHYMAL CELL, METHOD FOR PRODUCTION OF TOOTH, AND MESENCHYMAL CELL FOR FORMATION OF TOOTH

(75) Inventors: Takashi Tsuji, Nagareyama (JP); Ritsuko Morita, Abiko (JP)

(73) Assignee: Organ Technologies Inc., Tokyo (JP)

( * ) Notice: Subject to any disclaimer, the term of this patent is extended or adjusted under 35 U.S.C. 154(b) by 842 days.

(21) Appl. No.: 12/523,918

(22) PCT Filed: Jan. 18, 2008

(86) PCT No.: PCT/JP2008/050641
§ 371 (c)(1),
(2), (4) Date: Nov. 17, 2009

(87) PCT Pub. No.: WO2008/090826
PCT Pub. Date: Jul. 31, 2008

(65) Prior Publication Data
US 2010/0119997 A1 May 13, 2010

(30) Foreign Application Priority Data
Jan. 22, 2007 (JP) ................................. 2007-011805

(51) Int. Cl.
*C12N 5/00* (2006.01)
*C12N 5/02* (2006.01)
(52) U.S. Cl.
USPC ......................................... 435/377; 435/325
(58) Field of Classification Search
USPC ................................................ 435/325, 377
See application file for complete search history.

(56) References Cited

U.S. PATENT DOCUMENTS

| 5,942,435 | A * | 8/1999 | Wheeler ........................ 435/325 |
| 2002/0119180 | A1 | 8/2002 | Yelick et al. |
| 2004/0219489 | A1 | 11/2004 | Yelick et al. |
| 2006/0008902 | A1 * | 1/2006 | Pike et al. ...................... 435/371 |
| 2006/0024249 | A1 * | 2/2006 | Yelick et al. .................... 424/50 |
| 2006/0177386 | A1 * | 8/2006 | Ueda et al. ..................... 424/50 |
| 2007/0231275 | A1 | 10/2007 | Ueda |

FOREIGN PATENT DOCUMENTS

| CA | 2 610 474 A1 | 12/2006 |
| JP | A-2004-201612 | 7/2004 |
| JP | A-2004-331557 | 11/2004 |
| JP | A-2004-357567 | 12/2004 |
| WO | WO 2005/014070 A1 | 2/2005 |
| WO | WO 2005/111197 A1 | 11/2005 |
| WO | WO 2006/129672 A1 | 12/2006 |

OTHER PUBLICATIONS

Meirelles et al., 2003, British J. Haemotology, vol. 123, pp. 702-711.*
Brevini et al., 2010, Theriogenology, vol. 74, pp. 544-550.*
Paris et al. (2010, Theriogenology, vol. 74, pp. 516-524).*
Munoz et al. (2008, Theriogenology, vol. 69, pp. 1159-1164).*
Mitsiadis et al. (2003, PNAS, vol. 100(11), pp. 6541-6545).*
Peters et al. (1999, TIG, vol. 15(2), pp. 59-65).*
Miletich et al., 2003, Human Molecular Genetics, vol. 12(1), pp. R69-R73.*
European Search Report issued in European Patent Application No. 08703491.4 mailed on May 7, 2010.
Ohazama et al., "Stem-cell-based Tissue Engineering of Murine Teeth," Journal of Dental Research, 2004, vol. 83, No. 7, pp. 518-522.
Nakao et al., "The Reconstruction of Bioengineered Organ by Cell Manipulation," Micro-Nanomechatronics and Human Science, 2006, pp. 1-4.
Morita et al., "Pluripotent Stem Cells Developed into Regenerated Tooth by Organ Germ Method in Combination with Tooth Germ-Derived Epithelium," IEEE, 2007, pp. 203-207.
Young et al., "Tissue Engineering of Complex Tooth Structures on Biodegradable Polymer Scaffolds," *J. Dent. Res.*, vol. 81, No. 10, 2002, pp. 695-700.
Era et al., "Potentiality for Applying ES Cells to Clinical Medicine," *Saishin Igaku. Modern Medicine*, vol. 60, No. 8, 2005, pp. 1683-1687 (with partial translation).
Morita et al., "Induction of Organ Formation for a Tooth from Pluripotent Stem Cells," *Journal of the Japanese Association of Regenerative Dentistry*, vol. 5, No. 1, 2007 p. 74 (with translation).

(Continued)

*Primary Examiner* — Peter Paras, Jr.
*Assistant Examiner* — David A Montanari
(74) *Attorney, Agent, or Firm* — Oliff & Berridge, PLC

(57) ABSTRACT

The present invention provides a method for producing mesenchymal cells for production of mesenchymal cells for formation of a tooth, the method comprising: culturing totipotent stem cells in the presence of a differentiation inducer to produce a cell population after differentiation induction treatment, the cell population containing CD44-positive and CD29-positive cells or CD44-positive and CD106-positive cells; and selecting, from the cell population after the differentiation induction treatment, the CD44-positive and CD29-positive cells or CD44-positive and CD106-positive cells as the mesenchymal cells for the formation of the tooth. The present invention also provides a method for producing a tooth comprising: positioning, in a support carrier capable of retaining cells in a state of contacting therewith, a first cell mass substantially consisting of only either one of mesenchymal cells and epithelial cells and a second cell mass substantially consisting of only the other one of the mesenchymal cells and epithelial cells, the first and second cell masses being not mixed with each other but made to closely contact with each other; and culturing the first and second cell masses; wherein the mesenchymal cells comprise the mesenchymal cells for the formation of the tooth.

4 Claims, 7 Drawing Sheets

(56) References Cited

OTHER PUBLICATIONS

Mizokami et al., "Phenotypic and Functional Characterization of Amnion-Derived Mesenchymal Stem Cells," *Proceedings of the Japanese Society for Immunology*, vol. 37, 2007, p. 48, 1-C-W5-3-P.

Morita et al., "Development of a Regenerated Tooth with Mesenchymal Tissue Derived from Pluripotent Stem Cells," *Joint Annual Meeting of Molecular Bio. Society of Japan and Japanese Biochem. Society*, 2007, pp. 1P-0997, 1T8-9 (with translation).

You-Young et al., "Isolation and Characterization of Postnatal Stem Cells from Human Dental Tissues," *Tissue Engineering*, vol. 13, No. 4, 2007, pp. 767-773.

U.S. Appl. No. 11/921,233, filed Nov. 29, 2007 in the name of Tsuji et al.

Huey; "Application of Regenerative Medicine in Dental Disease;" *Regenerative Medicine*; Feb. 2008; pp. 91-104 (with partial translation).

Modino et al.; "Tissue engineering of teeth using adult stem cells;" *Archives of Oral Biology*; 2005; vol. 50; pp. 255-258.

Sonoyama et al.; "Mesenchymal Stem Cell-Mediated Functional Tooth Regeneration in Swine;" *PloS ONE*; Dec. 2006; vol. 79, No. 1; pp. 1-8.

Taiwanese Office Action dated Jan. 31, 2012 in Taiwanese Application No. 097102174 (with translation).

Australian Office Action dated Sep. 19, 2012 from Australian Patent Application No. 2008208433.

Zhao et al.; "Isolation and identification of chronic myelogenous leukemia bone marrow mesenchymal stem cells and their functional characteristics;" *Natl. Med. J. China*, 2005, vol. 85, No. 29, p. 2054-2057 (with Abstract).

Notice of Reasons for Rejection dated May 15, 2012 from Japanese Patent Application No. 2008-008772 (with translation).

* cited by examiner

SEQUENCE LISTING

```
<160> NUMBER OF SEQ ID NOS: 36

<210> SEQ ID NO 1
<211> LENGTH: 22
<212> TYPE: DNA
<213> ORGANISM: Artificial
<220> FEATURE:
<223> OTHER INFORMATION: primer Oct3/4-F

<400> SEQUENCE: 1
attgagaacc gtgtgaggtg ga                                              22

<210> SEQ ID NO 2
<211> LENGTH: 21
<212> TYPE: DNA
<213> ORGANISM: Artificial
<220> FEATURE:
<223> OTHER INFORMATION: primer Oct3/4-R

<400> SEQUENCE: 2
gcgccggtta cagaaccata c                                               21

<210> SEQ ID NO 3
<211> LENGTH: 23
<212> TYPE: DNA
<213> ORGANISM: Artificial
<220> FEATURE:
<223> OTHER INFORMATION: primer nanog-F

<400> SEQUENCE: 3
caagggtctg ctactgagat gct                                             23

<210> SEQ ID NO 4
<211> LENGTH: 20
<212> TYPE: DNA
<213> ORGANISM: Artificial
<220> FEATURE:
<223> OTHER INFORMATION: primer nanog-R

<400> SEQUENCE: 4
atcagggctg ccttgaagag                                                 20

<210> SEQ ID NO 5
<211> LENGTH: 20
<212> TYPE: DNA
<213> ORGANISM: Artificial
<220> FEATURE:
<223> OTHER INFORMATION: primer Slug-F

<400> SEQUENCE: 5
gaccctggct gcttcaagga                                                 20

<210> SEQ ID NO 6
<211> LENGTH: 20
<212> TYPE: DNA
<213> ORGANISM: Artificial
<220> FEATURE:
<223> OTHER INFORMATION: primer Slug-R

<400> SEQUENCE: 6
tattgcagtg agggcaagag                                                 20

<210> SEQ ID NO 7
<211> LENGTH: 21
<212> TYPE: DNA
```

```
<213> ORGANISM: Artificial
<220> FEATURE:
<223> OTHER INFORMATION: primer Pax3-F

<400> SEQUENCE: 7
caagctggag ccaatcaact g                                              21

<210> SEQ ID NO 8
<211> LENGTH: 17
<212> TYPE: DNA
<213> ORGANISM: Artificial
<220> FEATURE:
<223> OTHER INFORMATION: primer Pax3-R

<400> SEQUENCE: 8
gcggtgggag ggaatcc                                                   17

<210> SEQ ID NO 9
<211> LENGTH: 22
<212> TYPE: DNA
<213> ORGANISM: Artificial
<220> FEATURE:
<223> OTHER INFORMATION: primer Wnt1-F

<400> SEQUENCE: 9
cctacgcttc ctcatgaacc tt                                             22

<210> SEQ ID NO 10
<211> LENGTH: 20
<212> TYPE: DNA
<213> ORGANISM: Artificial
<220> FEATURE:
<223> OTHER INFORMATION: primer Wnt1-R

<400> SEQUENCE: 10
tggcgcatct cagagaacac                                                20

<210> SEQ ID NO 11
<211> LENGTH: 19
<212> TYPE: DNA
<213> ORGANISM: Artificial
<220> FEATURE:
<223> OTHER INFORMATION: primer Sox9-F

<400> SEQUENCE: 11
gaggccacgg aacagactc                                                 19

<210> SEQ ID NO 12
<211> LENGTH: 21
<212> TYPE: DNA
<213> ORGANISM: Artificial
<220> FEATURE:
<223> OTHER INFORMATION: primer Sox9-R

<400> SEQUENCE: 12
cagcgccttg aagatagcat t                                              21

<210> SEQ ID NO 13
<211> LENGTH: 17
<212> TYPE: DNA
<213> ORGANISM: Artificial
<220> FEATURE:
<223> OTHER INFORMATION: primer Sox5-F

<400> SEQUENCE: 13
gcgttggacg ggaaggt                                                   17
```

```
<210> SEQ ID NO 14
<211> LENGTH: 20
<212> TYPE: DNA
<213> ORGANISM: Artificial
<220> FEATURE:
<223> OTHER INFORMATION: primer Sox5-R

<400> SEQUENCE: 14
tccttttctg tccggcagtt                                              20

<210> SEQ ID NO 15
<211> LENGTH: 21
<212> TYPE: DNA
<213> ORGANISM: Artificial
<220> FEATURE:
<223> OTHER INFORMATION: primer Msx1-F

<400> SEQUENCE: 15
cagccctata gaaagcaagg a                                            21

<210> SEQ ID NO 16
<211> LENGTH: 20
<212> TYPE: DNA
<213> ORGANISM: Artificial
<220> FEATURE:
<223> OTHER INFORMATION: primer Msx1-R

<400> SEQUENCE: 16
cccctcagag caatgctttg                                              20

<210> SEQ ID NO 17
<211> LENGTH: 16
<212> TYPE: DNA
<213> ORGANISM: Artificial
<220> FEATURE:
<223> OTHER INFORMATION: primer Pax9-F

<400> SEQUENCE: 17
ggccaggcac cgaatg                                                  16

<210> SEQ ID NO 18
<211> LENGTH: 19
<212> TYPE: DNA
<213> ORGANISM: Artificial
<220> FEATURE:
<223> OTHER INFORMATION: primer Pax9-R

<400> SEQUENCE: 18
gccatgctgg atgctgaga                                               19

<210> SEQ ID NO 19
<211> LENGTH: 19
<212> TYPE: DNA
<213> ORGANISM: Artificial
<220> FEATURE:
<223> OTHER INFORMATION: primer Wnt5a-F

<400> SEQUENCE: 19
cgccatgaag aagcccatt                                               19

<210> SEQ ID NO 20
<211> LENGTH: 17
<212> TYPE: DNA
<213> ORGANISM: Artificial
<220> FEATURE:
<223> OTHER INFORMATION: primer Wnt5a-R
```

-continued

```
<400> SEQUENCE: 20
tccagcggtc cccaaag                                                  17

<210> SEQ ID NO 21
<211> LENGTH: 25
<212> TYPE: DNA
<213> ORGANISM: Artificial
<220> FEATURE:
<223> OTHER INFORMATION: primer Lhx8-F

<400> SEQUENCE: 21
aagtggagaa cggtaatggg attag                                         25

<210> SEQ ID NO 22
<211> LENGTH: 22
<212> TYPE: DNA
<213> ORGANISM: Artificial
<220> FEATURE:
<223> OTHER INFORMATION: primer Lhx8-R

<400> SEQUENCE: 22
gctttggatg attgacgtct tg                                            22

<210> SEQ ID NO 23
<211> LENGTH: 24
<212> TYPE: DNA
<213> ORGANISM: Artificial
<220> FEATURE:
<223> OTHER INFORMATION: primer BMP4-F

<400> SEQUENCE: 23
tcaagacacc atgattcctg gtaa                                          24

<210> SEQ ID NO 24
<211> LENGTH: 17
<212> TYPE: DNA
<213> ORGANISM: Artificial
<220> FEATURE:
<223> OTHER INFORMATION: primer BMP4-R

<400> SEQUENCE: 24
gctcgcgcct cctagca                                                  17

<210> SEQ ID NO 25
<211> LENGTH: 18
<212> TYPE: DNA
<213> ORGANISM: Artificial
<220> FEATURE:
<223> OTHER INFORMATION: primer Runx2-F

<400> SEQUENCE: 25
acggccctcc ctgaactc                                                 18

<210> SEQ ID NO 26
<211> LENGTH: 26
<212> TYPE: DNA
<213> ORGANISM: Artificial
<220> FEATURE:
<223> OTHER INFORMATION: primer Runx2-R

<400> SEQUENCE: 26
gggatctgta atctgactct gtcctt                                        26

<210> SEQ ID NO 27
<211> LENGTH: 16
<212> TYPE: DNA
```

<213> ORGANISM: Artificial
<220> FEATURE:
<223> OTHER INFORMATION: primer Dlx1-F

<400> SEQUENCE: 27
agccgagccc gagctt                                                         16

<210> SEQ ID NO 28
<211> LENGTH: 22
<212> TYPE: DNA
<213> ORGANISM: Artificial
<220> FEATURE:
<223> OTHER INFORMATION: primer Dlx1-R

<400> SEQUENCE: 28
cagccggtcc ttcctagaag tt                                                  22

<210> SEQ ID NO 29
<211> LENGTH: 20
<212> TYPE: DNA
<213> ORGANISM: Artificial
<220> FEATURE:
<223> OTHER INFORMATION: primer FGF10-F

<400> SEQUENCE: 29
tccctctggg tacggatctg                                                     20

<210> SEQ ID NO 30
<211> LENGTH: 20
<212> TYPE: DNA
<213> ORGANISM: Artificial
<220> FEATURE:
<223> OTHER INFORMATION: primer FGF10-R

<400> SEQUENCE: 30
tggtcggctc tcttgcataa                                                     20

<210> SEQ ID NO 31
<211> LENGTH: 18
<212> TYPE: DNA
<213> ORGANISM: Artificial
<220> FEATURE:
<223> OTHER INFORMATION: primer BMP7-F

<400> SEQUENCE: 31
cgctccaaga cgccaaag                                                       18

<210> SEQ ID NO 32
<211> LENGTH: 21
<212> TYPE: DNA
<213> ORGANISM: Artificial
<220> FEATURE:
<223> OTHER INFORMATION: primer BMP7-R

<400> SEQUENCE: 32
gctgctgttt tctgccacac t                                                   21

<210> SEQ ID NO 33
<211> LENGTH: 20
<212> TYPE: DNA
<213> ORGANISM: Artificial
<220> FEATURE:
<223> OTHER INFORMATION: primer beta Actin-F

<400> SEQUENCE: 33
tgacaggatg cagaaggaga                                                     20

```
<210> SEQ ID NO 34
<211> LENGTH: 20
<212> TYPE: DNA
<213> ORGANISM: Artificial
<220> FEATURE:
<223> OTHER INFORMATION: primer beta Actin-R

<400> SEQUENCE: 34
gctggaaggt ggacagtgag                                          20

<210> SEQ ID NO 35
<211> LENGTH: 20
<212> TYPE: DNA
<213> ORGANISM: Artificial
<220> FEATURE:
<223> OTHER INFORMATION: periostin primer -7

<400> SEQUENCE: 35
ggctgaagat ggttcctctc                                          20

<210> SEQ ID NO 36
<211> LENGTH: 20
<212> TYPE: DNA
<213> ORGANISM: Artificial
<220> FEATURE:
<223> OTHER INFORMATION: Periostin primer 573

<400> SEQUENCE: 36
gtacattgaa ggaataacca                                          20
```

METHOD FOR PRODUCTION OF MESENCHYMAL CELL, METHOD FOR PRODUCTION OF TOOTH, AND MESENCHYMAL CELL FOR FORMATION OF TOOTH

TECHNICAL FIELD

The present invention relates to a method for producing mesenchymal cells for formation of a tooth, to a method for producing a tooth, to and a mesenchymal cell for formation of a tooth.

BACKGROUND ART

A tooth is an organ having enamel in the outermost layer and dentin in the inner layer, both of which are hard tissues, odontoblasts inner side of the dentin, which produces dentin, and dental pulp in the central portion, and may be lost by dental caries, periodontal diseases or the like.

Teeth are functional units that are formed by induction during the developmental process of the fetal stage and constructed with plural cell types, and they are thought to be the same as organs or internal organs. Therefore, teeth could not be generated by stem cell system in which various cells are generated from a single stem cell such as a hematopoietic stem cell or a mesenchymal stem cell in the adult body. At results, teeth cannot be regenerated solely by stem cell transplantation (stem cell transplantation therapy) which is currently under development by regenerative medicine.

Therefore, studies have been conducted recently with a central focus on tooth regeneration by transplanting a reconstituted tooth germ obtained by reconstituting a tooth germ using isolated tooth germ cells.

For example, in *J. Dent. Res.*, 2002, Vol. 81(10), pp. 695-700, it is disclosed that a tooth-like tissue is regenerated by transplanting cells, such as epithelial cells isolated from a tooth germ and mesenchymal dental follicle cells, with a biodegradative carrier into an abdominal cavity of a rat.

As a method of regenerating a tooth germ, it is described, for example, in Japanese Patent Application Laid-open (JP-A) No. 2004-331557, that tooth germ cells isolated from a living body are cultured in the presence of biologically active substances such as fibroblast growth factors and the like. In JP-A No. 2004-357567, it is proposed that at least one type of cells selected from tooth germ cells and cells which can be differentiated into these tooth germ cells, both of them are isolated from a living body, are cultured along with a fibrin-containing carrier, and it is described that a "tooth" having a specific shape is formed by using a fibrin-containing carrier having the desired shape for the tooth germ.

In US Patent Application Publication No. 2002/0119180 and US Patent Application Publication No. 2004/0219489, a method of forming teeth is disclosed that includes seeding a cell mixture of a tooth germ containing dentin forming mesenchymal cells derived from dental pulp and epithelial cells which contribute to enamel formation, from the mandible of a 6 month-old pig, into a scaffold which is a solidified biodegradable polymer containing a polyglycolic acid/polyacetic acid copolymer; and transplanting it into an animal body. Here, it is described that a "tooth" having a specific shape is formed by using a scaffold having the desired shape for the tooth germ.

Further, in International Publication (WO) No. 2005/014070, a method of tooth regeneration for treating a patient with bone loss or damage is disclosed. According to this method, a bone is formed by seeding mesenchymal cells in a polyglycolic acid mesh carrier and then laminating the carrier with epithelial cells and collagen or wrapping it with an epithelial cell sheet. Further, in WO 2005/014070, a carrier is used to construct the shape of a bone.

In WO 2006/129672, a tooth producing method is described, the method including obtaining cell masses which are made of epithelial cells and mesenchymal cells from a dental germ, respectively; contacting these cell masses with each other in a collagen gel; culturing these cell masses under contacting conditions so as to obtain a tooth having a specific cell arrangement for a tooth.

However, in the above techniques, in order to regenerate a tooth or a tooth germ, tooth germ cells or cells capable of differentiating thereinto are obtained from a living body. In such a technique in which cells collected from a living body are used, the number of cells which can be obtained is sometimes insufficient. Further, the source of supply of the cells is sometimes limited.

To exert a function as a tissue, it is indispensable that multiple types of cells constituting the tissue be arranged (cell arrangement) at appropriate relative positions and have directionality as the tissue.

DISCLOSURE OF THE INVENTION

The present invention was made in view of the above-described circumstances and provides a method for producing a tooth and a mesenchymal cell for formation of a tooth.

The first aspect of the present invention provides a method for producing mesenchymal cells for the formation of a tooth, the method including: culturing totipotent stem cells in the presence of a differentiation inducer to produce a cell population after differentiation induction treatment, the cell population containing CD44-positive and CD29-positive cells or CD44-positive and CD106-positive cells; and selecting, from the cell population after the differentiation induction treatment, the CD44-positive and CD29-positive cells or CD44-positive and CD106-positive cells as the mesenchymal cells for formation of the tooth.

The second aspect of the present invention provides a method for producing a tooth including: arranging, in a support carrier, a first cell mass substantially consisting of only either one of mesenchymal cells and epithelial cells and a second cell mass substantially consisting of only the other one of the mesenchymal cells and epithelial cells, the first and second cell masses being not mixed with each other but made to closely contact with each other; and culturing the first and second cell masses in the support carrier; wherein the mesenchymal cells include the above-described mesenchymal cells for formation of a tooth.

The third aspect of the present invention provides mesenchymal cells for the formation of a tooth, which cells are induced from totipotent stem cells, and are CD44-positive and CD29-positive, or CD44-positive and CD106-positive.

According to the present invention, a method for producing mesenchymal cells by which a desired tooth may be effectively prepared in a large amount, and a method for producing a tooth wherein a tooth retaining a specific cell arrangement of enamel and dentin may be effectively produced in a large amount, may be provided.

BEST MODE FOR CARRYING OUT THE INVENTION

Method for Producing Mesenchymal Cells

Figure 1:
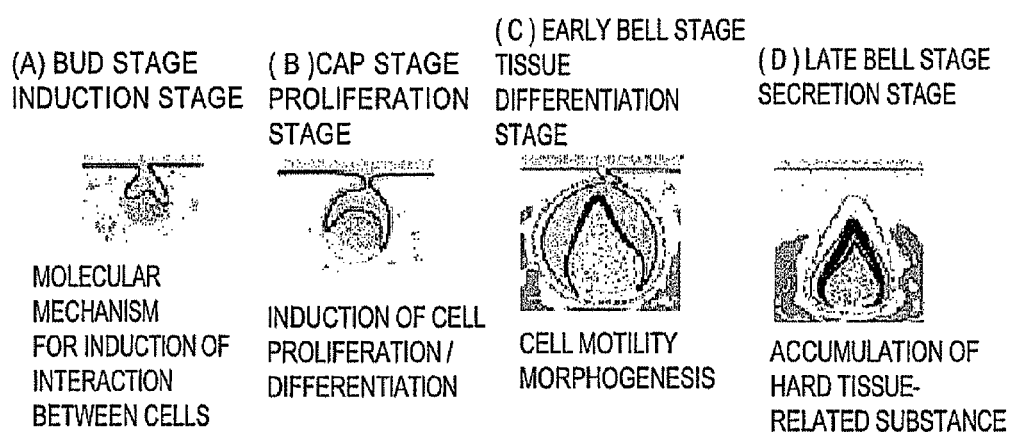
FIG. 1 is a schematic conceptual view showing the generation of a tooth germ.

The method of the present invention for producing mesenchymal cells is a method for producing mesenchymal cells for formation of a tooth, the method including: culturing totipotent stem cells in the presence of a differentiation inducer to produce a cell population after differentiation induction treatment, the cell population containing CD44-positive and CD29-positive cells or CD44-positive and CD106-positive cells; and selecting, from the cell population after the differentiation induction treatment, the CD44-positive and CD29-positive cells or CD44-positive and CD106-positive cells as the mesenchymal cells for formation of the tooth.

In the present invention, it was discovered that CD44-positive and CD29-positive cells or CD44-positive and CD106-positive cells obtained by differentiation induction of totipotent stem cells may be used as mesenchymal cells for the formation of a tooth. By this, mesenchymal cells necessary for preparation of a tooth may be obtained from sources other than a tooth or a tooth germ derived from a living body, and usage of a tooth or the like derived from a living body is not required for obtaining mesenchymal cells necessary for formation of a tooth. As a result, a necessary amount of mesenchymal cells may be easily obtained, in some cases, in a large amount, without having to take in to consideration circumstances such as an insufficient number of cells directly collected from a tooth germ or possible restrictions in the source of supply.

In the present invention, the term "tooth" means a tissue continuously having a layer of dentin inside and a layer of enamel outside, especially a tissue having directionality resulting from a crown and a root. The directionality of a tooth may be identified by arrangement of its crown and root. The crown and root may be visually confirmed based on their shapes, histological staining or the like. The crown means a part having a layer structure of enamel and dentin, and the enamel layer is absent in the root.

Dentin and enamel may be easily and morphologically identified by those skilled in the art by histological staining or the like. Enamel may also be identified by the presence of an ameloblast, which may be confirmed by the presence/absence of amelogenin. On the other hand, dentin may be identified by the presence of an odontoblast, which may be confirmed by the presence/absence of dentin sialoprotein. Confirmation of amelogenin and dentin sialoprotein may be carried out easily by a method well-known in the art, and examples of the method include in situ hybridization and staining with an antibody, or the like.

The mesenchymal cells of the present invention may first be used for forming a tooth germ in order to form a tooth.

In the present invention, the terms "tooth germ" and "tooth bud" are used to refer specifically to those distinguished based on the developmental stages described later. In this case, "tooth germ" means an early embryo of a tooth, which is destined to become a tooth in the future, and which is at a stage including the bud stage and the bell stage according to typical developmental staging of a tooth, and especially means such a tissue in which no accumulation of dentin and enamel is observed, which are characteristic to the hard tissue of a tooth. On the other hand, "tooth bud" means a tissue at a stage between the transitional stage from "tooth germ" used in the present invention, that is, the stage where the accumulation of dentin and enamel characteristic to the hard tissue of a tooth starts, and the stage before a tooth germinates from gum to exert typical functions of a tooth.

Development of a tooth from a tooth germ follows each of the bud stage, the cap stage, the early bell stage and the late bell stage as shown in FIG. 1 during the process of ontogeny. Here, at the bud stage, epithelial cells invaginate such that they wrap around mesenchymal cells, and when reaching the early bell stage and the late bell stage, the epithelial cell portion becomes the outer enamel and the mesenchymal cell portion begins to form dentin internally. Therefore, a tooth is formed from a tooth germ by cell-cell interaction between epithelial cells and mesenchymal cells.

In the present invention, "mesenchymal cell" means a cell derived from a mesenchymal tissue and "epithelial cell" means a cell derived from an epithelial tissue.

Further, in the present invention, "periodontal tissue" means alveolar bone and periodontal membrane formed mainly in the outer layer of a tooth. Alveolar bone and periodontal membrane may be morphologically and easily identified by those skilled in the art by histological staining or the like.

The mesenchymal cells of the present invention for forming a tooth will now be described.

The totipotent stem cells used to obtain the mesenchymal cells of the present invention for forming a tooth refer to cells having multidifferentiation potential by which two or more types of cells may be differentiated, and cells selected from the group consisting of embryonal carcinoma cells, embryonic stem cells and embryonic germ cells may preferably be used. Among these, embryonal carcinoma cells (hereinafter referred to as "EC cells") are more preferred from the viewpoint of availability. EC cells applicable to the present invention may be those derived from any tissue such as nerve, testicle or ovary. Examples of such an EC cell include an NCR-G3 cell and NTERA-2 cell derived from human, and cell lines derived from mice, such as a c-1300 cell, an F9 cell, an LT-2 cell, an OTT6050 cell, a PCC4 cell, a P19 cell, an METT-1 cell or an STT-3 cell. These cells may be appropriately selected depending on the intended use, from cells derived from various animals, for example, primates (e.g., humans and monkeys) and ungulates (e.g., pigs, cows and horses), which are mammals; and rodents (e.g., mice, rats and rabbits), which are small mammals. Examples of the embryonal carcinoma cell line derived from mouse include the cell lines described above and clones derived therefrom.

A medium which is normally used may be used for culturing the totipotent stem cells. Examples of the medium which may be used for culturing include media generally used for culturing animal cells, such as Dulbecco's modified Eagle's medium (DMEM). To this medium, serum for promoting growth of the cells may be added, or, as an alternative to the serum, a cell growth factor such as FGF, EGF or PDGF, or a known serum component such as transferrin may be added. In cases where serum is added, its concentration may be appropriately changed depending on the culture conditions, and may usually be 10%. For the cell culture, normal culture conditions, such as those for culture in an incubator at 37° C. under 5% $CO_2$, may be applied. An antibiotic(s) such as streptomycin may be added as appropriate.

In the present invention, differentiation induction treatment is carried out on the totipotent stem cells by culturing in the presence of a differentiation inducer. By this differentiation induction treatment, a cell population containing CD44-positive and CD29-positive cells or CD44-positive and CD106-positive cells is produced from the totipotent stem cells. It is sufficient if the cell population obtained by the differentiation induction treatment contains the above-described CD44-positive and CD29-positive cells or CD44-positive and CD106-positive cells, and both of these cells may also be contained.

Examples of the above differentiation inducer which may be used include any CD44-positive cell inducing factor which can at least induce differentiation into CD44-expressing cells from totipotent stem cells. Examples of such a CD44-positive cell inducing factor include neural crest cell-inducing factors, neural crest cell development-responsible factors and neural crest cell growth-promoting factors. A neural crest cell-inducing factor is a factor which may induce a totipotent stem cell to a neural crest cell or a cell derived therefrom (e.g., smooth muscle cell or cardiac muscle cell), and examples of the factor include dimethyl sulfoxide (DMSO), Dex, cAMP, hexamethylene bisacetamide, 5'-azacytidine, TGFβ and Noggin. Examples of a neural crest cell development-responsible factor include retinoic acid (RA), BMP-4, BMP-7, Shh, Wnt, FGF2, endothelin-1, endothelin-3, activinβA, PDGF and VEGF. Examples of a neural crest cell growth-promoting factor include FGF2, FGF8, FGF10, BMP-2, SCF and active vitamin D3. A neural crest cell-inducing factor, a neural crest cell development-responsible factor and a neural crest cell growth-promoting factor may not be clearly distinguished from each other, and each of these may be used solely, or two or more of these may be used in combination. Among these, DMSO and RA which can effectively produce the later-mentioned cell population of interest of the present invention are preferred, and these may be used solely or in combination.

These differentiation inducers may be added to the medium for totipotent stem cells to such a concentration at which differentiation induction is possible. Here, the concentration at which differentiation induction is possible varies depending on the types of the differentiation inducer and the types of the totipotent stem cells used.

In the case of DMSO, its concentration may be generally 0.5% by volume to 10% by volume, and, from the viewpoints of the survival rate of the cells upon the treatment and the yield of the cells of interest obtained by the culture, preferably 2.5% by volume to 5% by volume, more preferably 4% by volume to 5% by volume, relative to the volume of the medium. Differentiation of the totipotent stem cells can be sufficiently induced as long as the concentration is not less than 2.5% by volume, and the yield of the cells of interest is not extremely decreased as long as the concentration is not more than 5% by volume.

In the case of RA, its concentration may be generally 0.1 μM to 10 μM, and, from the viewpoints of the survival rate of the cells upon the treatment and the yield of the cells of interest obtained by the culture, preferably 0.5 μM to 5 μM, more preferably 0.5 μM to 2 μM in the medium. Differentiation of the totipotent stem cells can be sufficiently induced as long as the concentration is not less than 0.1 μM, and the yield of the cells of interest is not extremely decreased as long as the concentration is not more than 10 μM.

The differentiation induction treatment of the totipotent stem cells are carried out by culturing the totipotent stem cells in the presence of the above-described differentiation inducer(s). Although the time period of the differentiation induction treatment (culturing) varies depending on the concentration of the differentiation inducer(s) and the growth activity of the cells, it may be generally 2 hours to 3 days, and, from the viewpoints of the survival rate of the cells and the yield of the cells of interest obtained by the culture, preferably 6 hours to 24 hours. Sufficiently-differentiated cells can be effectively obtained as long as the time period is not less than 6 hours, and the yield of the cells of interest is not extremely decreased as long as the time period is not more than 24 hours.

There is a certain relationship between the time period of the differentiation induction treatment and the concentration of the differentiation inducer(s) in order to allow effective occurrence of the differentiation induction in the totipotent stem cells. That is, the time period of culturing in the presence of the differentiation inducer(s) (treatment time) varies depending on the concentration of the differentiation inducer(s) and the type of the differentiation inducer(s), but, in the case of a specific differentiation inducer, when the number of days of culture is fixed, there is generally a preferred optimum concentration range for the concentration. Further, in cases where the number of days of culture is decreased, the optimum concentration range shifts to the side of higher concentrations, while in cases where the number of days of culture is increased, the optimum concentration range shifts to the side of lower concentrations. Taking these factors into consideration, the differentiation induction effect can be exerted in a wide range of concentrations by adjusting the number of days of culture, and those skilled in the art can easily set the optimum concentration range at which the inducing effect may be exerted.

In a cell population after differentiation induction treatment obtained by the above differentiation induction treatment, a cell population containing CD44-positive and CD29-positive cells or CD44-positive and CD106-positive cells occur. The both cells may also be contained in the cell population. The cell population after the differentiation induction treatment is subsequently subjected to a selection treatment, in which the CD44-positive and CD29-positive cells or CD44-positive and CD106-positive cells are selected as mesenchymal cells for the formation of a tooth.

For selection of the cells, any method may be used as long as it is capable of selecting the mesenchymal cells according to the present invention as described above. Examples of such a selection method include selection methods based on gene expression patterns, cell surface antigens and morphology, and one or more of these methods may be used for selecting totipotent stem cells. The selection method is, from the viewpoint of effective selection of the cells, preferably a method using a cell sorter based on expression on the cell surface, and, in order to surely select the mesenchymal cells, usage of a combination of multiple methods, especially a combination of a gene expression pattern and a cell surface antigen, is preferred.

The mesenchymal cells for the formation of a tooth, which were selected in the present invention, are CD44-positive and, in addition, show the cell property of CD29-positive or CD106-positive. CD44 is known to be a membrane protein which is expressed as a hyaluronan receptor on the cell surface. On the other hand, CD29 is known to be a membrane protein which is expressed as an integrin 131 molecule on the cell surface, and has been reported to be weakly positive in EC cells and expressed in mesenchymal cells at the mRNA level. CD106 is known to be a VCAM-1 molecule which is known as an adhesion molecule, and often used as a marker for epithelial cells. Cells showing such properties may be used as the mesenchymal cells for the formation of a tooth, as described later.

The mesenchymal cells in the present invention for the formation of a tooth may be a population which is CD44-positive and at least either one of the antigens CD29 and CD106 is positive, and may also be a population containing triple-positive cells in which three types of the antigens, that is, CD44, CD29 and CD106, are all positive.

The mesenchymal cells of the present invention for the formation of a tooth may also be selected based on cell properties other than the above-described CD44, CD29 and CD106 cell expression antigens.

Examples of the other cell properties include other cell surface antigen patterns and gene expression patterns. Examples of the cell expression antigen patterns include CD14-negative, CD34-negative and CD45-negative, and these may be used solely or in combination. Examples of the gene expression patterns include, but not limited to, Slug expression, Wnt5a expression, Lhx8 expression, BMP4 expression, Pax3 expression, Pax9 expression, Msx1 expression, Oct3/4 non-expression, nanog non-expression, Sox9 non-expression and Sox5 non-expression, and these may be used solely or in combination.

The mesenchymal cells of the present invention for the formation of a tooth preferably express, in addition to the above-described CD44, CD29 and CD106, at least one gene selected from the group consisting of Slug gene, Pax3 gene, Msx1 gene and Pax9 gene, more preferably express the both Slug gene and Pax3 gene, still more preferably express all the four genes, because of their high tooth-forming potential.

For confirmation of these cell surface antigens and gene expression patterns, and for selection based thereon, various antibodies which recognize the surface antigens, nucleic acid sequences with which gene expression can be confirmed, and the like are used. All these antibodies and nucleic acid sequences are known and can be easily obtained. Confirmation and selection based on these surface antigens and gene expression patterns may be carried out using a method generally used in such applications, such as immunostaining by various antibodies, flow cytometry, cell sorters or RT-PCR.

In the production method of the present invention, cloning for obtaining a single mesenchymal cell may be used in combination with the above-described selection method. Examples of the cloning method include methods generally used for such a purpose, such as limiting dilution method, cell sorters or cloning rings. Although cloning may be carried out either before or after the selection by the above-described selection method, it is preferably carried out after the selection in order to obtain a mesenchymal cell(s) of interest effectively.

For obtaining a desired number of cells effectively in the selection step, a proliferation step may be provided before the selection step. In such a proliferation step, culturing of a cell population after differentiation induction is carried out using a medium for normal culture which does not contain a differentiation inducer. By this, cells of interest whose differentiation was induced may be allowed to proliferate to a prescribed cell number. As a result, the selection may be easily carried out with a sufficient number of the cells.

Although time period of such a proliferation step may be appropriately set based on the cell number and the cell state after the differentiation induction treatment, from the viewpoint of the concentration efficiency of the cells of interest, the time period may be generally 3 to 30 days, preferably 5 to 10 days. As a result, the mesenchymal cells of interest for the formation of a tooth become contained in the cell population to be subjected to the selection step, and, by subjecting such a cell population to the selection step, the mesenchymal cells of the present invention for the formation of a tooth may be effectively obtained in a large amount.

The mesenchymal cells obtained by the method of the present invention are used for the formation of a tooth. The formation of a tooth may be carried out by any method as long as the method uses mesenchymal cells of the present invention, and these cells are most preferably used in the following method of the present invention for producing a tooth.

The method of the present invention for producing a tooth will now be described.

[Method for Producing Tooth]

A preferred method for production of a tooth using the mesenchymal cells of the present invention for the formation of a tooth comprises: positioning, in a support carrier, a first cell mass substantially consisting of only either one of mesenchymal cells and epithelial cells and a second cell mass substantially consisting of only the other one of the mesenchymal cells and epithelial cells, the first and second cell masses being not mixed with each other but made to closely contact with each other (a positioning step); and culturing the first and second cell masses in the support carrier (a culturing step); wherein the mesenchymal cells include the above mesenchymal cells for the formation of the tooth.

In the present production method, since the mesenchymal cells and the epithelial cells are grown as cell masses in a support carrier under conditions whereby the masses are not mixed with each other but made to closely contact with each other, the cell-cell interaction may be effectively reproduced due to the close contact state, so that a tooth having a cell arrangement specific to a tooth, that is, dentin inside and enamel outside, may be obtained. Here, a cell mass substantially consisting of mesenchymal cells contains the mesenchymal cells of the present invention for forming a tooth, so that teeth having a specific cell arrangement can be efficiently produced in a large amount.

In the positioning step, the first cell mass and the second cell mass are brought into contact with each other and positioned in the support carrier.

Here, each of the first cell mass and the second cell mass is substantially composed of only the mesenchymal cells or only the epithelial cells. The cell mass substantially composed of only the mesenchymal cells contains the above-mentioned mesenchymal cells for the formation of a tooth. The cell mass containing the mesenchymal cells for formation of a tooth may be prepared by a preparation step according to the above-mentioned production method, and, on the other hand, the cell mass substantially composed of only the epithelial cells may be prepared independently from the cell mass substantially composed of only the mesenchymal cells (a first cell preparation step and a second cell preparation step).

The term "cell mass" means a state wherein cells are closely packed, and the cells may be in the state of a tissue or in the state of a cell mass (cell aggregate) prepared from the state of single cells. The term "substantially consists" means that the amount of matter included other than the cells of interest is as small as possible. Therefore, a cell mass consisting of epithelial cells may be a part of a tissue or a mass of single cells. The epithelial cells and the mesenchymal cells may also be both cell masses composed of single cells.

Either of the first cell mass and the second cell mass may be epithelial cells or mesenchymal cells. The numbers of cells constituting these cell masses vary depending on the species of the animal and on the type, hardness and size of the support carrier, and may be generally from $10^1$ to $10^8$ cells, and preferably from $10^3$ to $10^8$ cells per cell mass.

As long as the cell population substantially consisting of the mesenchymal cells contains the mesenchymal cells for the formation of a tooth, it may also contain other mesenchymal cells.

Examples of the mesenchymal cells other than the above mesenchymal cells may include mesenchymal cells derived from a tooth germ and from other than a tooth germ. Examples of the mesenchymal cells derived from other than a tooth germ include cells derived from other mesenchymal tissues in a living body, such as, preferably, bone marrow cells not containing blood cells and mesenchymal stem cells, more preferably, mesenchymal cells in the oral cavity, bone marrow cells inside the jawbone, mesenchymal cells derived from cranial neural crest cells, mesenchymal precursor cells which can generate the mesenchymal cells, and stem cells thereof.

The epithelial cells used in the present invention are preferably derived from a tooth germ so that they may reproduce the cell arrangement in a living body and effectively form a tooth having a specific structure and directionality, and preferably at a stage between the bud stage and the cap stage from the viewpoints of immaturity and homogeneity of the differentiation stage of the cells.

The epithelial cells may also be those derived from other than a tooth germ, and examples thereof include cells derived from other epithelial tissues in a living body. Preferred examples of the epithelial cells include epithelial cells of skin, mucosa and gingiva in the oral cavity, and more preferred examples of the epithelial cells include immature epithelial precursor cells which can produce differentiated, for example, keratinized or parakeratinized, epithelial cells such as skin, mucosa and the like. Examples of such immature epithelial precursor cells include non-keratinized epithelial cells and stem cells thereof.

In cases where cells are isolated from tissues for preparation of a cell mass, a tooth germ and other tissues may be collected from the jawbone or the like of various animals, for example, primates such as humans and monkeys and ungulates such as pigs, cows and horses, which are mammals; and rodents such as mice, rats and rabbits, which are small mammals. For the collection of the tooth germ and the tissue, a condition generally used for collecting a tissue may be applied without modification, and the tooth germ and the tissue may be collected under sterile conditions and stored in an appropriate preservation solution. Examples of a human tooth germ include the tooth germ of a third molar, which is the so-called wisdom tooth, as well as a fetal tooth germ, and, from the viewpoint of utilization of autogenous tissues, usage of the tooth germ of a wisdom tooth is preferred.

In cases where the above cells are prepared from a tissue, for example, a tooth germ, the tooth germ isolated from its surrounding tissue is first divided into a tooth germ mesenchymal tissue and a tooth germ epithelial tissue based on their shapes. Since the tooth germ tissue can be structurally identified under the microscope, it can be easily isolated by tearing or cutting using dissecting scissors, forceps or the like. Isolation of the tooth germ mesenchymal tissue and the tooth germ epithelial tissue from the tooth germ can be easily carried out based on their shapes, by tearing or cutting using injection needles, tungsten needles, forceps or the like.

Preferably, an enzyme may be used to easily isolate the tooth germ cells from their surrounding tissue and/or to isolate an epithelial tissue and a mesenchymal tissue from the tooth germ tissue. Examples of the enzyme used in such applications include dispase, collagenase and trypsin.

The cells constituting the cell masses may be prepared from the state of a collected tissue into the state of single cells. In the preparation step, an enzyme may be used to make the cells easily dispersible as single cells. Examples of such an enzyme include dispase, collagenase and trypsin. In this case, for the isolation of epithelial cells from an epithelial tissue, it is preferred to perform trypsin treatment and DNase treatment after collagenase treatment. On the other hand, for the isolation of mesenchymal cells from a mesenchymal tissue, it is preferred to perform collagenase treatment and trypsin treatment simultaneously and to finally perform DNase treatment. In this case, the DNase treatment is performed in order to prevent a decrease in the amount of recovered cells due to cell aggregation caused by DNA released into the solution when a part of the cells are damaged by the enzyme treatment and the cell membrane is lysed.

The cells constituting the cell masses may be those which have been subjected to preliminary culture prior to the positioning step in order to obtain a sufficient number of each kind of the cells. For the cell culture, a condition, such as temperature, generally used for culture of animal cells may be applied without modification.

As the medium used for the culture, a medium generally used for animal cell culture, such as Dulbecco's Modified Eagle Medium (DMEM), may be used, and serum for promotion of cell proliferation may be added, or, as an alternative to the serum, a cellular growth factor such as FGF, EGF or PDGF or a known serum component such as transferrin may be added. In cases where serum is added, its concentration may be changed appropriately depending on the culture conditions, and may usually be 10% by volume. For the cell culture, normal culture conditions, such as those for culture in an incubator at 37° C. under 5% $CO_2$, may be applied. An antibiotic such as streptomycin may be added as appropriate.

In cases where this preliminary culture is applied to the mesenchymal cells, the culture may be one that doubles as the above-mentioned culture for proliferating the mesenchymal cells for the formation of a tooth, or may be one carried out after the selection step, or may be both of these.

From the viewpoint of not changing properties of the cells, the preliminary culture of the mesenchymal cells and the above-mentioned culture for simply proliferating the mesenchymal cells for the formation of a tooth are preferably carried out in a medium which does not contain the above-mentioned differentiation inducer.

With regard to positioning of the cell masses in the positioning step, the first and second cell masses are positioned in the support carrier which can maintain the contacting state of the cells. In this case, the cell masses do not mix with each other. Thus, since the cell masses are positioned without being mixed with each other, a boundary surface is formed between the cell masses. Such a mode of positioning is called "compartmentalization" as appropriate in the present specification.

The support carrier used here may be one in which cells can be cultured, and preferably a mixture with the above medium. Examples of such a support carrier include collagen, agarose gel, carboxymethyl cellulose, gelatin, agar, hydrogel, Cellmatrix (trade name), Mebiol Gel (trade name), Matrigel (trade name), elastin, fibrin, laminin, an extracellular matrix mixture, polyglycolic acid (PGA), polylactic acid (PLA) and lactic acid/glycolic acid copolymer (PLGA). These support carriers may have a hardness with which the cells can be virtually maintained at the locations where they are positioned in the support carrier, and examples of the support carrier include those in the forms of a gel, fiber and solid. Among these, from the viewpoint that gels such as extracellular matrix mixtures tend to provide appropriate hardness and retentive capacity, collagen, agarose gel, carboxymethyl cellulose, gelatin, agar, hydrogel, Cellmatrix, Mebiol Gel, Matrigel, an extracellular matrix mixture, elastin, fibrin and laminin are more preferred. In this case, the hardness with which the cells can be virtually maintained at their locations may be hardness which is applicable to three-dimensional culture, that is, a hardness with which the position of the cells can be maintained while hypertrophy of the cells due to their proliferation is not inhibited, and such hardness can be easily determined.

Further, in this case, the support carrier may have a thickness sufficient for allowing growth of the first and second cell masses inside the carrier, and the thickness may be appropriately set depending on the size of the tissue of interest, and the like.

Further, the support carrier may have a retentive capacity whereby the cells can maintain their contacting state without being dispersed. As used herein, the "contacting state" is preferably a closely-packed (high density) state which ensures the cell-cell interaction within each cell mass and between the cell masses, and such a high density state in a cell aggregate enables culturing of the cells with at a degree of retention, for example, with which a stronger contacting state than a state of simply touching can be maintained. For example, in the case of collagen, appropriate hardness is provided for usage at a final concentration of 2 to 3 mg/ml, that is, a concentration which exerts a jelly strength of 120 g to 250 g based on the method according to JIS-K6503-1996 (measured as the load necessary for depressing by 4 mm using a plunger with a diameter of 123 mm). The jelly strength is not limited, and other types of support carriers may also be preferably used as the support carrier of the present invention as long as these have the same strength based on the same evaluation method. Further, a support carrier having hardness corresponding to the desired jelly strength may be obtained by mixing one or more kinds of support carriers.

A high density state means a density almost equivalent to the density at which a tissue is constructed, for example, in the case of the cell masses, $5 \times 10^7$ to $1 \times 10^9$ cells/ml at the time of cell positioning, preferably $1 \times 10^8$ to $1 \times 10^9$ cells/ml to ensure the cell-cell interaction without impairing the cell activity, and most preferably $2 \times 10^8$ to $8 \times 10^8$ cells/ml. In order to prepare a cell mass having such a cell density, it is preferred to mass and precipitate cells by centrifugation since this conveniently enables achievement of the high density without impairing the cell activity. Such centrifugation may be carried out at a revolution speed equivalent to a centrifugal force of 300 to 1200×g, which will not adversely affect the survival of the cells, and preferably 500 to 1000×g, for 3 to 10 minutes. Centrifugation at lower than 300×g may lead to insufficient precipitation of the cells and the cell density may become low, while centrifugation at higher than 1200×g may cause damage to the cells, and therefore both of these cases are not preferred.

In cases where high density cells are prepared by centrifugation, the centrifugation is normally carried out after preparing a suspension of single cells in a container such as a tube used for cell centrifugation, and the supernatant is removed to the greatest extent possible, leaving the cells as the precipitates. It is preferred that the container such as a tube be siliconized from the viewpoint of complete removal of the supernatant.

In cases where the precipitates are prepared by centrifugation, these may be directly positioned inside the support carrier. Here, the volume of components other than the cells of interest (for example, a culture medium, a buffer solution, the support carrier or the like) is preferably not more than the volume of the cells, and most preferably, components other than the cells of interest are not contained. In such a high density cell mass, cells are in close contact with each other and the cell-cell interaction may be effectively exerted. Especially, in cases where a cell mass containing only an extremely small amount of components other than the cells of interest is positioned inside the support carrier, the cells further mass due to solidification of the support carrier and the like, to provide a state wherein the cells are more tightly packed.

In cases where the cells are used in a tissue state, it is preferred to remove components other than the cells of interest, such as connective tissues, by performing an enzyme treatment or the like. In cases where there are many components other than the cells of interest, for example, in cases where the volume of the other components is not less than that of the cells, the cell-cell interaction may not be sufficiently exerted, which is not preferred.

The closer the contact between the first cell mass and the second cell mass, the better, and it is especially preferred that the second cell mass be positioned such that it presses against the first cell mass. Further, wrapping around the first cell mass and the second cell mass with a solid which does not inhibit a culture medium or oxygen permeation is also effective in making the contact between the cell masses closer. It is also preferred to add a high-density cell suspension to a solution having a different viscosity to position the cell suspension therein, followed by solidification of the solution as is, since this may conveniently achieve maintenance of contacting of the cell. Here, in cases where the first cell mass is an mass of single tooth germ mesenchymal cells and the second cell mass is a tooth germ epithelial tissue, it is preferred to position the enamel knot of the tooth germ epithelial tissue in contact with the first cell mass, but the present invention is not limited to this.

In cases where the support carrier is in the form of a gel, solution or the like, the positioning step may be followed by the solidification step, by which the support carrier is solidified. By the solidification step, cells positioned inside the support carrier may be fixed inside the support carrier. For solidification of the support carrier, conditions generally used for solidification of the support carrier may be applied without modification. For example, in cases where a solidifiable compound such as collagen is used for the support carrier, solidification can be achieved under conditions generally applied, for example, by being left to stand at the culture temperature for several minutes to several tens of minutes. By this, bonds between the cells inside the support carrier can be fixed and made robust.

In the culturing step of the production method of the present invention, a first cell mass and a second cell mass are cultured inside the support carrier. In this culturing step, the cell-cell interaction is effectively exerted by the first cell mass and the second cell mass which are in close contact with each other, to reconstruct a tissue, namely, a tooth.

The culturing step may be carried out such that the contacting state between the first cell mass and the second cell mass is maintained by the support carrier, and may be culturing by the support carrier which simply has the first and the second cell masses, or culturing in the presence of other animal cells.

The time period of the culture varies depending on the number of cells positioned in the support carrier and the states of the cell masses, as well as on the conditions under which the culturing step is carried out, and may be generally 1 to 300 days, preferably 1 to 120 days in order to form a tooth having enamel outside and dentin inside, and preferably 1 to 60 days from the viewpoint of providing the tooth quickly. Further, to form a tooth having a periodontal tissue, the time period may be generally 1 to 300 days, preferably 1 to 60 days.

In cases where the culture was performed only with the support carrier, the culture can be performed under normal conditions used for culturing of animal cells. Here, in general, the conditions for culturing of animal cells can be applied without modification, and the above-mentioned conditions can be applied without modification. Further, serum derived from mammals, and various cellular factors which are known to be effective in growth and differentiation of these cells may be added to the culture. Examples of such cellular factors include FGF and BMP.

Further, it is preferred to use organ culture from the viewpoint of gas exchange and nutrient supply for tissues and cell masses. In organ culture, generally, culturing is performed by floating porous membrane on a culture medium suitable for growth of animal cells and placing a cell mass embedded in a support carrier on the membrane. The porous membrane used herein is preferably a membrane having many pores with the diameter of 0.3 to 5 µm, and specific examples thereof include Cell Culture Insert (trade name) and Isopore Filter (trade name).

Performing the culture in the presence of other animal cells is preferred because a tooth having a specific cell arrangement can be formed at an early stage in response to the actions of various cytokines and the like from the animal cells. Such culture in the presence of other animal cells may be performed by culturing ex vivo using isolated cells or cultured cells.

Further, the support carrier having the first and the second cell masses may be transplanted to a living body to carry out culture in vivo. Such culture in vivo is especially preferred since a tooth and/or a periodontal tissue can be formed at an early stage. In this case, the first and the second cell masses are transplanted together with the support carrier into the living body.

Preferred examples of animals which can be used for this application include mammals such as humans, pigs and mice, and the animal is more preferably derived from the same species as that of the tooth germ tissue. In cases where a human tooth pan tissue is transplanted, it is preferred to use a human, or a mammal other than human which was altered to be immunodeficient. In order to develop an organ or tissue of animal cells as normally as possible, examples of a site in a living body suitable for such in vivo growth preferably include subrenal capsule, mesentery (omentum), subcutaneous and oral cavity.

The time period for the growth according to the transplantation varies depending on the size of the explant at the time of the transplantation and the size of the tooth to be developed, and may be typically 3 to 400 days. For example, the time period of subrenal capsule transplantation is preferably 7 to 60 days from the viewpoints of tooth regeneration and the size of the tooth to be developed at the site of the transplantation, although it varies depending on the size of the explant to be transplanted and the size of the tooth to be regenerated.

Ex vivo culture (preculture) may be performed prior to the transplantation to the living body. The preculture is preferred since the bonds between cells and the bond between the first and the second cell masses can be made strong, to make the cell-cell interaction stronger. As a result, the total growth period can be shortened.

The preculture period may be either short or long. A longer period of time, for example, 3 days or more, preferably 7 days or more, is preferred since a tooth bud can be developed from a tooth germ during this period and thus the time period until a tooth is formed after the transplantation can be shortened. For example, in the case of organ culture for transplantation beneath the subrenal capsule, the time period of preculture is preferably 1 to 7 days in order to efficiently regenerate a tooth.

A tooth produced according to the production method of the present invention has a tooth-specific cell arrangement (structure) having dentin inside and enamel outside, and preferably has directionality, that is, has a tip (crown) and a root of a tooth. By having at least such specific cell arrangement, and preferably by having directionality in addition to the cell arrangement, functions of a tooth can be exerted. Therefore, the produced tooth can be widely used as an alternative to a tooth. Particularly when the mesenchymal cells and epithelial cells derived from an autogenous tooth germ are used, problems caused by rejection can be avoided. Generally, it is also possible to avoid problems caused by rejection in cases where the cells are derived from a tooth germ of another person having a matching transplantation antigen.

The teeth produced by the production method of the present invention may be in the form of a set of teeth having a tooth-specific cell arrangement.

Since such a set of teeth is constituted by multiple teeth having a tooth-specific cell arrangement, each tooth can be separated from the set of teeth and used as an explant of a single tooth as described below. As a result, teeth as explants can be efficiently prepared.

To obtain a set of teeth constituted by multiple teeth, it is preferred that both of the first and the second cell mass be constituted by single cells in order to facilitate reinduction of tooth germs to develop multiple teeth.

The culturing step may be either organ culture or subrenal capsule culture as described above, and, when the obtained tooth is used as an explant, it is preferred to perform organ culture in which there is no contact with other cells of animals and the entire procedure can be processed in vitro.

Further, in the production method of the present invention, the culture period may be extended until a periodontal tissue is formed. By this, it is possible to form, in addition to a tooth itself, a periodontal tissue such as alveolar bone and periodontal membrane, which support and stabilize teeth on the jaw bone. As a result, a practicable tooth can be provided after the transplantation.

To produce a periodontal tissue, the step to isolate the periodontal tissue obtained by the above culture may be carried out after the above culturing step, to obtain only the periodontal tissue. Isolation of the periodontal tissue may be performed according to any method in which the periodontal tissue formed during the culturing step can be separated from a tooth, and examples of such a method include separation with forceps or the like and partial digestion by enzymes.

The tooth and the periodontal tissue obtained according to the present invention may be used as an explant and may also be preferably used in a research for elucidation of the developmental process of a tooth, so that they may be used as an effective research tool for development of tissues related to teeth in the future.

In cases where the tooth or the periodontal tissue obtained is used as an explant, the culturing step according to the production method is preferably performed as organ culture in which there is no contact with other animal cells and the entire procedure can be processed in vitro.

A method for transplantation of a tooth is also included in the present invention. This method for transplantation includes: a step of obtaining the above-described set of teeth; a step of separating each tooth from a complex of teeth; and a step of transplanting the separated tooth while aligning a tooth such that it has the same directionality as other teeth at the site of the transplantation.

In this way, multiple teeth having a specific cell arrangement and directionality can be obtained simultaneously and tooth transplantation can be performed efficiently.

The tooth according to the present invention can also be applied to therapies or treatments of various symptoms accompanying by loss of or damage to teeth, and examples of the symptoms include dental caries, marginal periodontitis (alveolar pyorrhea), loss of teeth by periodontal diseases, tooth breakage or avulsion caused by accidents or the like.

In other words, the therapeutic method of the present invention includes transplanting of the tooth and/or periodontal tissue obtained by the production method of the present invention into the site of tooth loss and/or damage. By this, the above-described symptoms at the site of tooth loss and/or damage can be treated and/or alleviated.

Another therapeutic method of the present invention includes carrying out only the culturing step of the present invention, or carrying out the positioning step and the culturing step at the site of tooth loss and/or damage. In this case, the surrounding tissue at the site of tooth loss and/or damage itself may be applied as a support carrier in addition to the support carriers mentioned above. Thus, due to cytokines or the like from the surrounding tissues in the living body, therapy or the like of the site of the loss and/or damage can be carried out more quickly.

EXAMPLES

Examples of the present invention will now be described, but the present invention is not limited thereto. "%" in Examples is by weight (mass) unless otherwise specified.

Example 1

1. Method for Culturing EC Cells

As the EC cells, AT805 cells (a clone derived from OTT6050, EC cells of the strain129; obtained from the Cell Bank, RIKEN Bioresource Center) were used. Culturing of AT805 cells was performed using Dulbecco's modified Eagle's medium (DMEM; manufactured by SIGMA or Kohjin Bio Co. Ltd.) supplemented with 10% by volume fetal calf serum (FCS: manufactured by JRH, JBS or Hyclone) and 55 µM 2-mercaptoethanol (manufactured by GIBCO). EC cells were usually plated at a concentration of 5 to $8 \times 10^5$ cells per 100 mm dish, and complete replacement of the medium and passage culture were repeated every other day. In passage culture, the cells were washed once with HCMF buffer (pH7.4; 10 mM Hepes, 136.9 mM NaCl, 0.34 mM $Na_2HPO_3$, 13.9 mM glucose, 5.37 mM KCl), and 5 ml of an enzyme solution wherein trypsin-EDTA.2Na (manufactured by GIBCO) was dissolved at the final concentration of 0.025% was then added thereto, followed by an enzyme treatment at 37° C. for 1 minute. Subsequently, an equal amount of DMEM supplemented with 10% FCS was added to disperse the cells, and the cells were then precipitated and collected by centrifugation. The collected cells were resuspended and plated on a new culture dish to carry out passage culture.

2. Differentiation Induction of EC Cells and Collection of Cells

EC cells collected by trypsin treatment were suspended in DMEM supplemented with 10% by volume FCS and dimethylsulfoxide (DMSO: manufactured by SIGMA) at the final concentration of 0.5 to 5% by volume, and plated at the concentration of $1.0 \times 10^6$ cells per 100 mm dish. Culture was carried out under 5% $CO_2$ at 37° C., and after 14 hours, the cells were washed once with HCMF buffer, followed by replacement of the medium with DMEM supplemented with 10% by volume FCS.

Figure 2A:
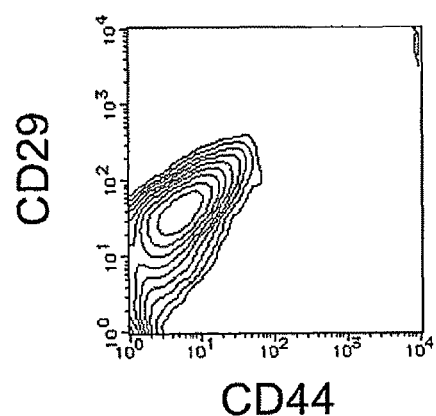
FIG. 2A shows the state of double staining of CD44 and CD29 of EC cells according to Example 1 of the present invention.
Figure 2B:
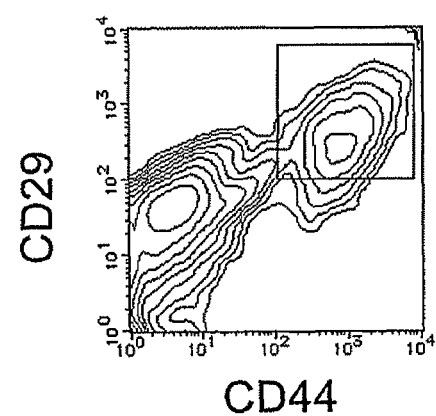
FIG. 2B shows the state of double staining of CD44 and CD29 of the cells at 6 days after DMSO treatment, according to Example 1 of the present invention.
Figure 2C:
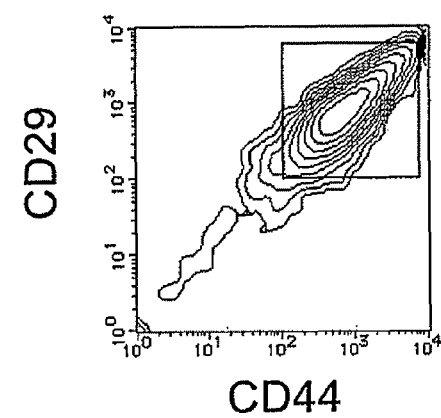
FIG. 2C shows the state of double staining of CD44 and CD29 of the selected CD44-positive and CD29-positive cells according to Example 1 of the present invention.

EC cells treated with DMSO was continuously cultured for 6 days (19 days only in the case of 5% by volume DMSO) with replacement of a half amount of the medium every 3 days with DMEM supplemented with 10% by volume FCS, and observation was carried out as appropriate. When a cell population containing undifferentiated cells was grown, it washed once with HCMF buffer and then suspended by addition of $Ca^{2+}/Mg^{2+}$-free PBS(−)(EDTA/BSA-PBS) supplemented with 3 mM EDTA and 0.5% BSA, followed by centrifugation to collect cells as precipitates. The cells were resuspended in EDTA/BSA-PBS and then subjected to double staining with an FITC-labeled anti-CD44 antibody (CD44-FITC: manufactured by BD Pharmingen) and a PE-labeled anti-CD29 antibody (CD29-PE: manufactured by BD Pharmingen). A CD44-positive and CD29-positive cell fraction was isolated using a cell sorter, Epics ALTRA (manufactured by Beckman Coulter), to obtain an EC cell fraction wherein differentiation was induced by a DMSO treatment and undifferentiated EC cell were excluded (see FIG. 2). These cells were designated DMSO-EC cells.

Proportions of DMSO-EC cells upon treatment with various concentrations of DMSO are shown in Table 1. As shown in Table 1, it was revealed that CD44-positive and CD29-positive cells increased depending on the DMSO concentration at which the treatment was performed. With regard to the EC cells treated with 5% by volume DMSO, it was found that, while most cells died immediately after the treatment, which necessitated a larger number of days of culture after the treatment than in the cases of treatment with other concentrations, the proportion of CD44-positive and CD29-positive cells obtained after the culture was high.

Thereafter, experiments were carried out with the cells obtained using 5% by volume DMSO.

TABLE 1

| Concentration of DMSO (v/v %) | Culture days (day) | Cell number (×10$^7$ cells) | CD44-positive and CD29-positive cells(%) |
|---|---|---|---|
| 0 | | | |
| 0.5 | 6 | 1.15 | 0.3 |
| 1.0 | 6 | 1.19 | 0.5 |
| 2.5 | 6 | 1.64 | 13.7 |
| 5.0 | 19 | 2.83 | 93.0 |

Cloning of DMSO-EC Cells

Cloning of DMSO-EC cells were carried out by isolation of colonies using cloning rings or by limiting dilution method.

In collection of cells using the cloning rings, DMSO-EC cells were plated on a culture dish at a low concentration (about 100 cells) and, when the number of the cells in a colony formed by growth of the cells became not less than 10, sterilized silicone grease was applied to one end of the cloning ring, which was then attached to the bottom surface of the dish after removal of the medium such that the cloning ring encloses the colony. Thereafter, a trypsin treatment was performed inside the cloning ring, and the cells were collected. Grown cells were sequentially subjected to scaling up of the culture to obtain a clone.

In obtaining a clone by limiting dilution method, DMSO-EC cells obtained by the above method were washed once with HCMF buffer, and subsequently, the cells were collected by a trypsin treatment. The numbers of the collected cells were counted, and the cells were then plated on a 96-well culture plate so as to achieve 1 cell/200 µl/well (explanation). They were confirmed to be single colonies 3 to 5 days later. Thereafter, their culture was continued with replacement of a half amount of the medium every 5 days. Grown cells were sequentially subjected to scaling up of the culture to obtain a clone.

By this, clone 1 (DMSO-EC clone 1: Clone #1) and clone 2 (DMSO-EC clone 2: Clone #2) derived from DMSO-EC cells were obtained.

Example 2

Properties of DMSO-EC Cells (1) Phase Contrast Micrograph

Morphology of the above obtained clones 1 and 2 and morphology of EC cells, DMSO-EC cells, and ATDC5 cells (obtained from the Cell Bank, RIKEN Bioresource Center) which are EC cell-derived cartilage precursor cells were each observed under a phase-contrast microscope.

As a result, it was observed that EC cells in a colony were small and grew at a high density, and the fringe of the colony was raised, and therefore that these cells had a typical totipotent stem cell-like morphology. On the other hand, with regard to DMSO-EC cells, the clones 1 and 2 of DMSO-EC cells, and ATDC5 cells, the area of each cell constituting a colony was large, and the cells formed a monolayer characteristic to adhesive cells, therefore showing a morphology clearly different from the characteristic morphology of EC cells. Such morphology as adhesive cells is similar to that of mesenchymal cells rather than to that of EC cells.

(2) Expression of Various Genes

Expression of various genes in EC cells, DMSO-EC cells, the clones 1 and 2 of DMSO-EC cells, and ATDC5 cells were analyzed by real-time PCR (RT-PCR) and expression of marker genes were examined.

Extraction of total RNAs from EC cells, DMSO-EC cells, the clones 1 and 2 of DMSO-EC cells, and ATDC5 cells were carried out using TRIzol Reagent (manufactured by Invitrogen). The culture medium of the cells to be analyzed was removed, and 2 ml of TRIzol Reagent was directly added dropwise to the 100 mm culture dish. After sufficient mixing of the cells with Cell Scraper (manufactured by Falcon), the resulting mixture was collected into an Eppendorf tube and subjected to homogenization with a Polytron homogenizer (manufactured by Polytron). The subsequent operations before the RNA extraction step were carried out according to the manufacturer's instruction included in the kit. Total RNAs extracted from cells/tissues were dissolved in DEPC-treated water, and their concentrations were calculated using a spectrophotometer, followed by storage at −30° C.

Using the total RNAs extracted from the cells as templates, cDNAs as templates for real-time PCR (RT-PCR) analysis were synthesized. Synthesis of the cDNAs was carried out using ReverTra Ace (TOYOBO), and the operation was carried out according to the manufacturer's instruction included in the kit.

PCR and analysis were carried out using ABI PRISM 7000 (manufactured by Applied Biosystems). SYBR Premix Ex Taq (manufactured by TAKARA) was used as the polymerase, and β-actin was used as an endogenous control. To a 96-well plate for RT-PCR, 13 µl of SYBR Premix Ex Taq (manufactured by TAKARA), 2 µl of 20-fold diluted cDNA reaction solution, 5 µl each of primers at a concentration of 1 µM and 5 µl of sterilized water were added per sample to prepare a reaction system with the final volume of 25 µl, and a PCR reaction was carried out according to a conventional method. Further, a calibration curve was prepared for each gene by carrying out control reactions to enable individual quantification. The sequences of the primers used for the analysis are shown in Table 2 and Table 3.

The gene expression level was normalized against the expression level of β-actin in each group of cells, and comparisons were made based on the relative expression levels assuming the constant expression level of β-actin. The results are shown in Table 4.

TABLE 2

| | | |
|---|---|---|
| Oct3/4-F | ATTGAGAACCGTGTGAGGTGGA | (SEQ ID NO: 1) |
| Oct3/4-R | GCGCCGGTTACAGAACCATAC | (SEQ ID NO: 2) |
| nanog-F | CAAGGGTCTGCTACTGAGATGCT | (SEQ ID NO: 3) |
| nanog-R | ATCAGGGCTGCCTTGAAGAG | (SEQ ID NO: 4) |
| Slug-F | GACCCTGGCTGCTTCAAGGA | (SEQ ID NO: 5) |
| Slug-R | TATTGCAGTGAGGGCAAGAG | (SEQ ID NO: 6) |
| Pax3-F | CAAGCTGGAGCCAATCAACTG | (SEQ ID NO: 7) |
| Pax3-R | GCGGTGGGAGGGAATCC | (SEQ ID NO: 8) |
| Wnt1-F | CCTACGCTTCCTCATGAACCTT | (SEQ ID NO: 9) |
| Wnt1-R | TGGCGCATCTCAGAGAACAC | (SEQ ID NO: 10) |
| Sox9-F | GAGGCCACGGAACAGACTC | (SEQ ID NO: 11) |
| Sox9-R | CAGCGCCTTGAAGATAGCATT | (SEQ ID NO: 12) |
| Sox5-F | GCGTTGGACGGGAAGGT | (SEQ ID NO: 13) |
| Sox5-R | TCCTTTTCTGTCCGGCAGTT | (SEQ ID NO: 14) |
| Msx1-F | CAGCCCTATAGAAAGCAAGGA | (SEQ ID NO: 15) |
| Msx1-R | CCCCTCAGAGCAATGCTTTG | (SEQ ID NO: 16) |
| Pax9-F | GGCCAGGCACCGAATG | (SEQ ID NO: 17) |
| Pax9-R | GCCATGCTGGATGCTGAGA | (SEQ ID NO: 18) |

TABLE 3

| | | |
|---|---|---|
| Wnt5a-F | CGCCATGAAGAAGCCCATT | (SEQ ID NO: 19) |
| Wnt5a-R | TCCAGCGGTCCCCAAAG | (SEQ ID NO: 20) |
| Lhx8-F | AAGTGGAGAACGGTAATGGGATTAG | (SEQ ID NO: 21) |
| Lhx8-R | GCTTTGGATGATTGACGTCTTG | (SEQ ID NO: 22) |
| BMP4-F | TCAAGACACCATGATTCCTGGTAA | (SEQ ID NO: 23) |
| BMP4-R | GCTCGCGCCTCCTAGCA | (SEQ ID NO: 24) |
| Runx2-F | ACGGCCCTCCCTGAACTC | (SEQ ID NO: 25) |
| Runx2-R | GGGATCTGTAATCTGACTCTGTCCTT | (SEQ ID NO: 26) |
| Dlx1-F | AGCCGAGCCCGAGCTT | (SEQ ID NO: 27) |
| Dlx1-R | CAGCCGGTCCTTCCTAGAAGTT | (SEQ ID NO: 28) |
| FGF10-F | TCCCTCTGGGTACGGATCTG | (SEQ ID NO: 29) |
| FGF10-R | TGGTCGGCTCTCTTGCATAA | (SEQ ID NO: 30) |
| BMP7-F | CGCTCCAAGACGCCAAAG | (SEQ ID NO: 31) |
| BMP7-R | GCTGCTGTTTTCTGCCACACT | (SEQ ID NO: 32) |
| βActin-F | TGACAGGATGCAGAAGGAGA | (SEQ ID NO: 33) |
| βActin-R | GCTGGAAGGTGGACAGTGAG | (SEQ ID NO: 34) |

TABLE 4

| Gene | DMSO- EC | DMSO-EC #1 | DMSO-EC #2 | ATDC5 | Type of maker |
|---|---|---|---|---|---|
| Oct3/4 | 100 | 0 | 0 | 0 | 0 | Undifferentiated |
| nanog | 377 | 0 | 0 | 0 | 0 | cells |
| Slug | 2 | 92 | 100 | 83 | 94 | Neural crest |
| Pax3 | 0 | 57 | 92 | 100 | 3 | cells |
| Wnt1 | 0 | 35 | 67 | 32 | 0 | |
| Msx1 | 48 | 91 | 100 | 91 | 1 | Mesenchymal |
| Pax9 | 1 | 50 | 67 | 100 | 12 | cells of a tooth |
| Wnt5a | 5 | 100 | 86 | 75 | 5 | |
| Lhx8 | 4 | 93 | 100 | 54 | 0 | |
| BMP4 | 0 | 100 | 68 | 97 | 39 | |
| Runx2 | 0 | 44 | 53 | 53 | 100 | |
| Dlx1 | 7 | 47 | 43 | 46 | 100 | |
| Fgf10 | 4 | 15 | 12 | 18 | 5 | |
| BMP7 | 26 | 3 | 1 | 2 | 0 | |
| Sox9 | 1 | 10 | 10 | 10 | 100 | Cartilage cells |
| Sox5 | 7 | 4 | 4 | 5 | 58 | |

As shown in Table 4, expression of Oct3/4 and Nanog, which are marker genes for undifferentiated stem cells, were detected only in EC cells, but not detected in EC cells obtained by DMSO treatment, clone cells thereof, and ATDC5 cells. Expression of Slug, Pax3 and Wnt1, which are marker genes for neural crest cells, were not observed in EC cells; expression of Slug was observed in all the cell groups other than EC cells; and expression of Pax3 and Wnt1 were observed in all the DMSO-EC cell groups other than EC cells and ATDC5 cells, although there were differences among their expression levels.

Thus, DMSO-EC cells and the cloned cells thereof were suggested to have occurred by differentiation induction from undifferentiated stem cells into neural crest cells, and, according to properties of their gene expression, they were revealed to be Oct3/4-negative, Nanog-negative, Slug-positive, Pax3-positive and Wnt1-positive cells.

On the other hand, with regard to marker groups for mesenchymal cells of a tooth, any gene other than Msx1 and BMP-7 was not expressed in EC cells, although Msx1, Pax9, Wnt5a and Lhx8 were specifically and highly expressed in DMSO-EC cells and the cloned cells thereof. Expression of BMP4, Runx2 and Dlx1 were observed in DMSO-EC cells and the cloned cells thereof, and ATDC5 cells, although there were some differences among their expression levels.

Expression of Sox9 and Sox5, which are marker genes specific to cartilage cells, were high only in ATDC5 cells, and therefore DMSO-EC cells and the cloned cells thereof were judged as cells undifferentiated to cartilage cells.

Therefore, it was obvious that EC cells were induced to differentiate by DMSO into neural crest cell-like or mesenchymal cell-like cells.

Example 3

Evaluation of Tooth-Forming Potential of Cells Whose Differentiation was Induced from Ec Cells Differentiation potentials into odontoblast and tooth dentin-forming potentials of DMSO-EC cells and the cloned cells thereof obtained by the present invention were tested as follows.
(1) Preparation of Tooth Germ Epithelial Tissue
From the embryo of a C57BL/6 mouse (purchased from SLC) at the embryonic age of 14.5 days, a lower incisor tooth germ tissue was isolated by a conventional method under the microscope. The isolated lower incisor tooth germ tissue was washed with PBS(−), and treated with an enzyme solution supplemented with 1.2 U/ml (final concentration) Dispase II (Roche, Mannheim, Germany) at room temperature for 12.5 minutes, followed by 3 times of washing with DMEM (Sigma, St. Louis, Mo.) supplemented with 10% FCS (JRH Biosciences, Lenexa, Kans.). Subsequently, a DNase I solution (Takara, Siga, Japan) was added such that the final concentration of 70 U/ml is achieved to disperse the tooth germ tissue, and a tooth germ epithelial tissue was surgically separated using a 25 G injection needle (Terumo, Tokyo, Japan).

(2) Preparation of Reconstructed Tooth Germ

Preparation of a Reconstructed Tooth Germ was Carried Out Using the Above Prepared tooth germ epithelial tissue and, as the mesenchymal cells, one of the cell groups to be evaluated, that is, EC cells, DMSO-EC cells, or the DMSO-EC clone 1 or 2, was used. Each of the cell groups to be evaluated which is used for reconstruction of a tooth germ was collected from a dish by a trypsin treatment. The cells to be evaluated which were suspended in DMEM (Sigma) supplemented with 10% FCS (JRH) were placed in a 1.5 ml microtube (Eppendorf, Hamburg, Germany) to which silicone grease was applied, and the cells were collected by centrifugation (580×g) as precipitates. After removal of the culture supernatant as much as possible, centrifugation was carried out again, and the culture medium remaining around the precipitates of the cells was completely removed using GELoader Tip 0.5-20 µL (manufactured by Eppendorf) while observing under a stereomicroscope to prepare each cell group to be evaluated which is used for preparation of a reconstructed tooth germ.

To a petri dish to which silicone grease was applied, 30 µl of 2.4 mg/ml Cellmatrix type I-A (manufactured by Nitta Gelatin Inc.) was added dropwise to prepare a collagen gel drop. To this solution, 0.2 µl to 10.3 µl of the above cells to be evaluated were applied using a 0.1-10 µl pipette tip (manufactured by Eppendorf) to prepare a cell aggregate as a high-density cell mass (cell density: $2 \times 10^8$ cells/ml). Subsequently, using a 10 µl pipette tip, a tooth germ epithelial tissue or a tooth germ mesenchymal tissue was applied to the same gel drop, and, using a tungsten needle, the surface of the tooth germ-derived epithelial tissue which originally contacted a mesenchymal tissue was brought into close contact with the cell aggregate of the cells to be evaluated. Thereafter, by solidifying the gel drop, the bonds between the tooth germ tissue and the cells to be evaluated were made stronger to prepare a high-density reconstructed tooth germ.

This will now be described referring to FIG. 3.

Figure 3A:
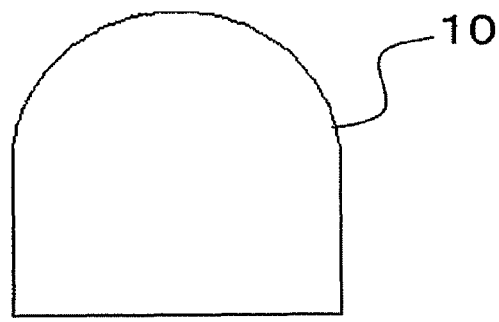
FIG. 3A is a schematic conceptual vies showing the procedure according to Examples of the present invention for reconstruction of a tooth germ using mesenchymal cells and epithelial cells derived from a tooth germ, and showing the state of a gel pack before cell arrangement.
Figure 3B:
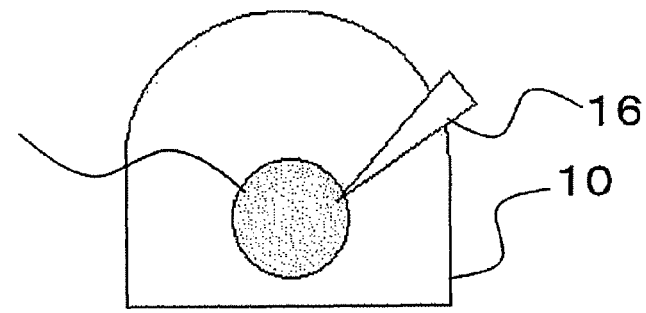
FIG. 3B is a schematic conceptual view showing the procedure according to Examples of the present invention for reconstruction of a tooth germ using mesenchymal cells and epithelial cells derived from a tooth germ, and showing the state of positioning of a first cell mass in a gel pack.
Figure 3C:
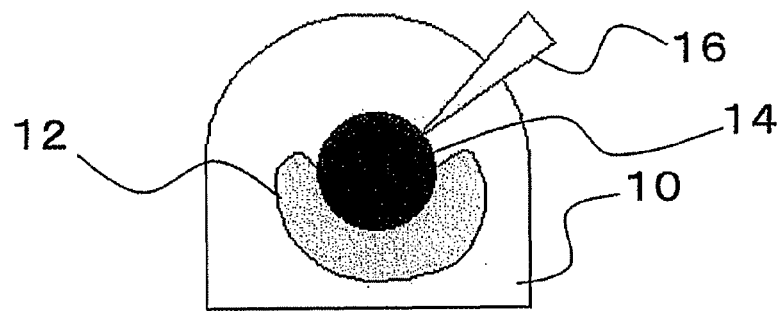
FIG. 3C is a schematic conceptual view showing the procedure according to Examples of the present invention for reconstruction of a tooth germ using mesenchymal cells and epithelial cells derived from a tooth germ, and showing the state of positioning of a second cell mass in a gel pack.
Figure 3D:
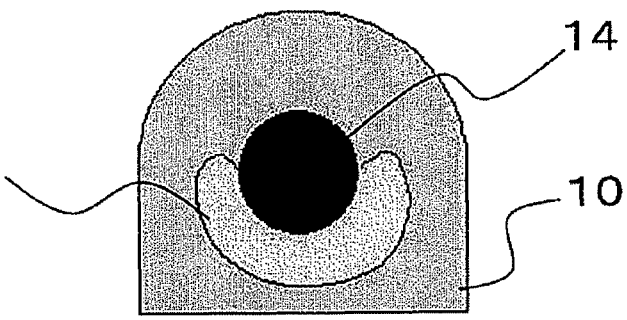
FIG. 3D is a schematic conceptual view showing the procedure according to Examples of the present invention for reconstruction of a tooth germ using mesenchymal cells and epithelial cells derived from a tooth germ, and shows the solidified state of a gel pack in which the first cell mass and the second cell mass are positioned.

The cell aggregate 12 which was previously positioned in the gel drop 10 (see FIG. 3A) with the pipette tip 16 constitutes a sphere in the gel drop 10 (see FIG. 3B). Then, by pressing the cell aggregate 14 thereinto, the spherical cell aggregate 12 is often crushed to wrap the cell aggregate 14 (see FIG. 3C). Thereafter, by solidifying the gel drop 10, bonds between the cells become strong (see FIG. 3D).

(3) Organ Culture of Reconstructed Tooth Germ

The high-density reconstructed tooth germ prepared in the gel was left to stand in a $CO_2$ incubator for 10 minutes to solidify Cellmatrix type I-A (Nitta Gelatin). A culture vessel was prepared such that DMEM (manufactured by Sigma) supplemented with 10% by volume FCS (manufactured by JRH), 0.1 mg/ml L-ascorbic acid (manufactured by Sigma) and 2 mM L-glutamine (manufactured by GIBCO) is in contact with Cell Culture Inserts (PET membrane having a pore size of 0.4 µm; manufactured by BD). The reconstructed tooth germ was transferred, together with the surrounding gel which is the support carrier, onto the membrane of Cell Culture Inserts in the culture vessel, to carry out organ culture.

Usually, in cases where development of a tooth was analyzed by organ culture, 14 days of culture was carried out. When organ culture was carried out, a reconstructed tooth germ was isolated 10 to 30 days after transplantation, and fixed with 4% paraformaldehyde-phosphate buffer for 6 hours, followed by 24 hours of neutral decalcification using 4.5% EDTA solution (pH 7.4). Thereafter, paraffin embedding was carried out according to a conventional method to prepare 10 µm sections. For a histological analysis, hematoxylin eosin staining (HE staining) was carried out according to a conventional method.

Evaluation by Organ Culture

In the case of a high-density reconstructed tooth germ of a lower incisor tooth germ epithelial tissue and EC cells, at the age of 14.5 days, the reconstructed tooth germ was enlarged due to abnormal growth of the EC cells, and, also in HE staining, odontoblasts and dentin derived from mesenchymal cells of a tooth were not observed.

In contrast, in DMSO-EC cells and the DMSO-EC clones 1 and 2, interaction with the epithelial tissue was induced and, also under a phase contrast micrograph, tissue induction was observed in the same manner as in organ culture of a tooth germ. Further, in any of DMSO-EC cells and the DMSO-EC clones 1 and 2, it was confirmed from HE-stained images that a reconstructed tooth germ having enamel outside and dentin inside may be formed, so that formation of the tissue structure specific to a tooth was shown to be possible.

By these results, it was evident that, due to interaction with tooth germ epithelial cells, DMSO-EC cells and the DMSO-EC clones 1 and 2 differentiate into odontoblasts which constitute the mesenchymal tissue of a tooth, and can produce dentin which is specific to a tooth. Further, it was evident that a tooth with a specific tissue structure having: enamel outside; dentin inside; internal dental pulp cells; and a tip and a root; could be formed also in organ culture by the high-density reconstructed tooth germ method.

Example 4

Method for Subrenal Capsule Transplantation

Thereafter, from DMSO-EC cells, cells of the DMSO-EC clones 1 and 2, and fetal lower incisor tooth germ epithelial cells at the age of 14.5 days, high-density reconstructed tooth germs were prepared, and the obtained reconstructed tooth germs were transplanted to the subrenal capsule of C57BL6 mice (obtained from CLEA Japan, Inc.) to evaluate their tooth-forming potentials.

Reconstructed tooth germs prepared in the same manner as in Example 3 were subjected to organ culture for 48 hours to 96 hours, and then transplanted to the subrenal capsule of NOD-SCID mice (obtained from Charles River) of 8 weeks old together with the surrounding gel to promote ectopic development of teeth for the analysis.

In the case of transplantation to the subrenal capsule, the reconstructed tooth germ was isolated together with the surrounding renal tissue on Day 10 to 30 after the transplantation. The isolated tissue was fixed with 4% paraformaldehyde-phosphate buffer for 6 hours, and 24 hours of neutral decalcification was carried out using 4.5% EDTA solution (pH 7.4). Thereafter, paraffin embedding was carried out according to a conventional method to prepare 10 µm sections. For a histological analysis, HE staining was carried out according to a conventional method.

(1) Evaluation by Subrenal Capsule Transplantation

Figure 4A:
FIG. 4A is an HE-stained image of a tooth germ according to Example 4 of the present invention prepared from a tooth germ epithelial tissue and a tooth germ mesenchymal cell (magnification: ×100).
Figure 4B:
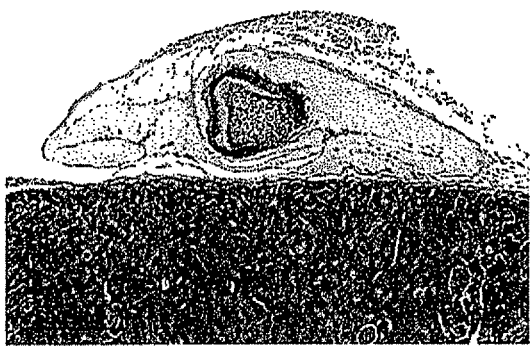
FIG. 4B is an HE-stained image of a tooth germ according to Example 4 of the present invention prepared from a tooth germ epithelial tissue and DMSO-EC cells (magnification: ×100).
Figure 4C:
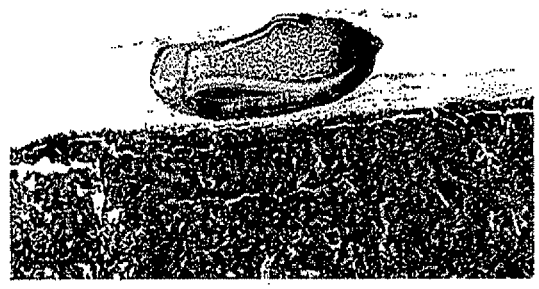
FIG. 4C is an HE-stained image of a tooth germ according to Example 4 of the present invention prepared from a tooth germ epithelial tissue and DMSO-EC cloned cells (magnification: ×100).

In the case of subrenal capsule transplantation, when fetal incisor tooth germ epithelial cells at the age of 14.5 days were transplanted, a tooth with a characteristic structure having dentin inside and enamel outside could be developed after a time period of 16 days by subrenal capsule transplantation (see FIG. 4). In the cases of reconstructed tooth germs by: a tooth germ epithelial tissue and tooth germ mesenchymal cells derived from a fetal incisor tooth germ at the age of 14.5 days (see FIG. 4A); the tooth germ epithelial tissue and DMSO-EC cells (see FIG. 4B); and the tooth germ epithelial tissue and a DMSO-EC clone (clone #1; see FIG. 4C); on Day 14 after subrenal capsule transplantation, ameloblasts and enamel outside, and dentin and odontoblasts inside thereof were easily identified as in the case where a normal tooth germ was transplanted to the subrenal capsule as it is. The resulting tooth had a tip and a root, showing the same structure as that of a normally-developed tooth.

The frequency of the formation of a tooth was 0% in EC cells and ATDC cells, while 51.3±8.8% in DMSO-EC cells, 23.3%±16.7% in the DMSO-EC clone 1, and 33.3%±47.1% in the DMSO-EC clone 2.

From these results, it became clear that DMSO-EC cells and the DMSO-EC clones 1 and 2 can differentiate into odontoblasts which constitute a tissue derived from tooth mesenchyme, and can produce dentin which is a hard tissue of a tooth. Further, it became clear that a tooth with the specific tissue structure can be formed by the high-density reconstructed tooth germ method with DMSO-EC cells or the DMSO-EC clones 1 or 2 also in subrenal capsule transplantation.

(2) In Situ Hybridization

A tooth germ epithelial tissue derived from a fetal incisor tooth germ at the age of 14.5 days and DMSO-EC cells were transplanted to the subrenal capsule, and, with a tissue isolated after 14 days, in situ hybridization was carried out to analyze expression of mRNAs of amelogenin, which is a constituent molecule of enamel, and that of dentin sialophosphoprotein (DSPP), which is a constituent element of dentin, as well as expression of mRNA of periostin, which is a gene specific to periodontal membrane.

A reconstructed tooth germ on Day 14 after subrenal capsule transplantation was isolated and fixed with 4% paraformaldehyde-phosphate buffer for 6 hours, followed by 24 hours of neutral decalcification using 4.5% EDTA solution (pH 7.4). Thereafter, the resultant was sequentially soaked in 12.5% sucrose solution and 25% sucrose solution, and embedded in OCT compound (manufactured by SAKURA Finetechnica). Subsequently, 10 μm sections were prepared by cryostat (manufactured by Leica).

The above sections were treated with PBS(−) containing Protease K (Nacalai tesque, Kyoto, Japan) at the final concentration of 2 μg/ml for 10 minutes, and fixed with PBS(−) containing paraformaldehyde (Nacalai tesque) at the final concentration of 4% for 10 minutes. After treating the resultants with diethylpyrocarbonate (DEPC)-treated water supplemented with 1.325% triethanolamine, 0.0175N HCl (Wako) and 0.25% acetic anhydride (all the values indicate the final concentrations) for 10 minutes, these were washed 3 times with PBS(−) for 5 minutes. After treating the resultants with DEPC water supplemented with 1.5% (v/v) triethanolamine (Nacalai tesque), 0.33N HCl (Wako) and 0.25% (v/v) acetic anhydride (Nacalai tesque) for 10 minutes, these were washed twice with 2×SSC for 10 minutes. A probe for periostin (GenBank accession no. NM_015784), which is a gene specific to periodontal membrane, was prepared by DIG labeling of a cDNA fragment obtained by PCR using the sense primer (−7; ggctgaagatggttcctctc: SEQ ID NO:35) and the antisense primer (573; gtacattgaaggaataacca: SEQ ID NO:36).

In situ hybridization was carried out according to a conventional method, and coloring was then carried out with an anti-DIG alkaline phosphatase (AP) Fab fragment (Roche) and NBT/BCIP Stock Solution (Roche), followed by analysis with Axio Imager A.1 (Zeiss) and AxioCam MRc5 (Zeiss).

From the results, expression of amelogenin mRNA in ameloblasts and expression of DSPP mRNA in odontoblasts, respectively, were observed in HE-stained images. Further, expression of periostin mRNA was observed. Thus, mRNAs of the respective molecules involved in formation of the hard tissues were clearly and appropriately expressed in cells responsible for their production. Further, since periostin, which is expressed in periodontal membrane, was detected, formation of a periodontal tissue was suggested.

Example 5

Induction by Retinoic Acid (1) Method for Differentiation Induction of EC Cells for Obtaining CD44-Positive and CD29-Positive Cells AT805 cells collected by a trypsin treatment in the same manner as in Example 1 were plated at a concentration of $1.0 \times 10^6$ cells per 100 mm dish, and, on the next day, the medium was replaced with DMEM supplemented with 10% by volume FCS, which was also added with retinoic acid (manufactured by SIGMA) at a final concentration of 0 to 10.0 μM, to stimulate the cells. After 72 hours of culture, the cells were washed twice with HCMF buffer, and the whole medium was replaced with DMEM supplemented with 10% by volume FCS only.

(2) Obtaining CD44-Positive and CD29-Positive Cells after RA Treatment

Figure 5A:
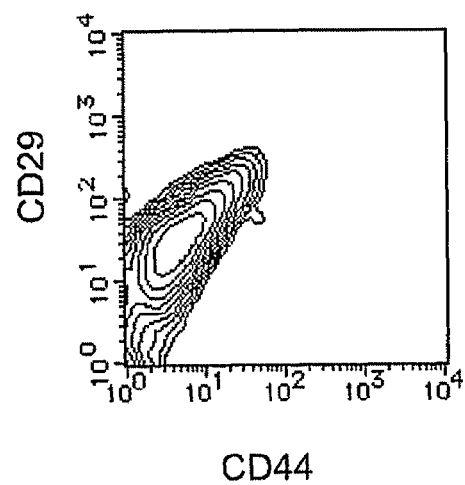
FIG. 5A shows the state of double staining of CD44 and CD29 of EC cells according to Example 5 of the present invention.
Figure 5B:
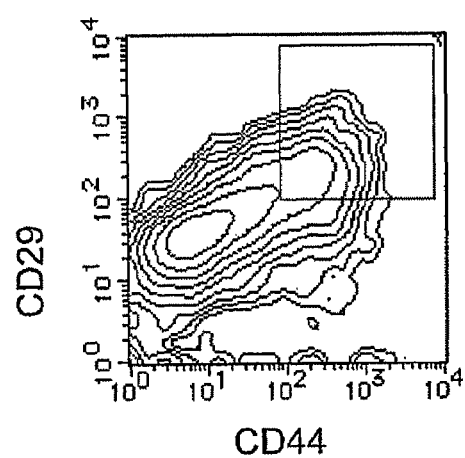
FIG. 5B shows the state of double staining of CD44 and CD29 of cells at 7 days after RA treatment, according to Example 5 of the present invention.
Figure 5C:
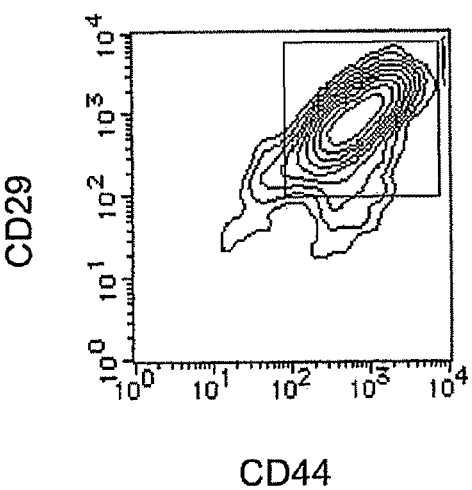
FIG. 5C shows the state of double staining of CD44 and CD29 of the selected CD44-positive and CD29-positive cells according to Example 5 of the present invention.

Culturing was continued for 7 days with replacement of a half amount of the medium every 3 days with DMEM supplemented with 10% by volume FCS, and observation was carried out as appropriate. A cell population grown after the RA treatment, which contains undifferentiated cells, was washed once with HCMF, and 3 mM EDTA-0.5% BSA-PBS(−) was added thereto, followed by incubation thereof at 37° C. After collecting cells, the cells were subjected to double staining with CD44 FITC (BD Pharmingen) and CD29 (BD Pharmingen) PE to separate and obtain CD44-positive and CD29-positive cells using Epics ALTRA (Beckman Coulter), and thus a cell population after exclusion of undifferentiated cells, which cell population is composed of only differentiated cells, was obtained. These cells were designated RA-EC cells. The results are shown in FIG. 5.

Further, proportions of RA-EC cells upon treatment with various concentrations of RA are shown in Table 5. As shown in Table 5, it was revealed that the proportions of the CD44-positive and CD29-positive cells vary depending on the RA concentration at which the treatment was performed.

Expression of genes in the CD44-positive and CD29-positive cells after the RA treatment were confirmed in the same manner as in Example 2(2), and these cells were revealed to be Oct3/4-negative, Nanog-negative, Slug-positive, Pax3-positive and Wnt1-positive as in the case of DMSO-EC cells.

TABLE 5

| Concentration of RA (μM) | Culture days (day) | Cell number (×10⁶ cells) | CD44-positive and CD29-positive cells (%) |
| --- | --- | --- | --- |
| 0 | | | |
| 0.5 | 7 | 1.5 | 10.8 |
| 1.0 | 7 | 1.1 | 10.0 |
| 2.0 | 7 | 1.3 | 11.3 |
| 5.0 | 7 | 0.5 | 11.5 |
| 10.0 | 7 | 0.7 | 10.4 |

Figure 6:
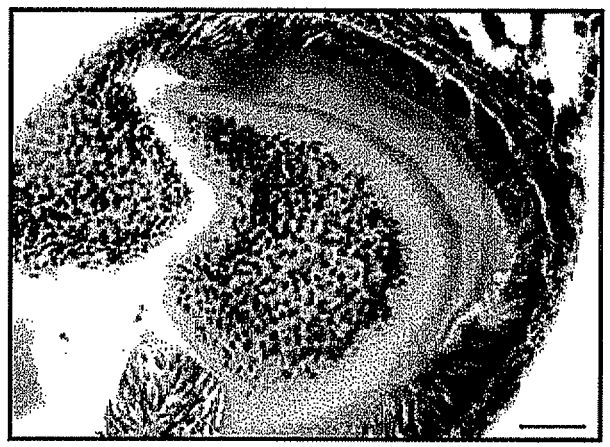
FIG. 6 is an HE-stained image of a tooth germ prepared from CD44-positive and CD106-positive cells obtained by RA treatment in Example 5 of the present invention and a tooth germ epithelial tissue (magnification: ×200, the bar represents 50 μm).

(3) Evaluation of Tooth-forming Potential of CD44-Positive and CD29-Positive Cells after RA Treatment Using CD44-positive and CD29-positive cells (RA concentration: 2 μM) obtained as above, tooth germ reconstruction and organ culture were carried out in the same manner as in Example 3 for evaluation. After 14 days of organ culture, the cells differentiated into odontoblasts corresponding to a mesenchymal tissue of a tooth, due to the interaction with tooth germ epithelial cells. Further, by the high-density reconstructed tooth germ method, a tooth with a tooth-specific tissue structure, having enamel outside and dentin inside and internal dental pulp cells, was formed (see FIG. 6).

Further, when expression of amelogenin, DSPP and periostin were confirmed with the CD44-positive and CD29-positive cells after the RA treatment in the same manner as in Example 4(2), their respective mRNAs were observed as in the case of DMSO-EC. Thus, formation of a periodontal tissue containing a hard tissue and periodontal membrane was suggested.

Example 6

(1) Method for Differentiation Induction of EC Cells for Obtaining CD44-Positive and CD106-Positive Cells AT805 cells collected by a trypsin treatment in the same manner as in Example 1 were plated at a concentration of $1.0 \times 10^6$ cells per 100 mm dish, and, on the next day, the medium was replaced with DMEM supplemented with 10% by volume FCS, which also was added with RA (manufactured by SIGMA) at a final concentration of 2 μM to stimulate the cells. After 72 hours of culture, the cells were washed twice with HCMF buffer, and the whole medium was replaced with DMEM supplemented with 10% by volume FCS only. On the next day, the cells were washed twice with HCMF buffer and dead cells were removed, followed by further continuation of the culture in DMEM supplemented with 10% by volume FCS only. Thereafter, the culture was carried out for 7 days with replacement of the medium every other day.

(2) Obtaining CD44-Positive and CD106-Positive Cells

Figure 7A:
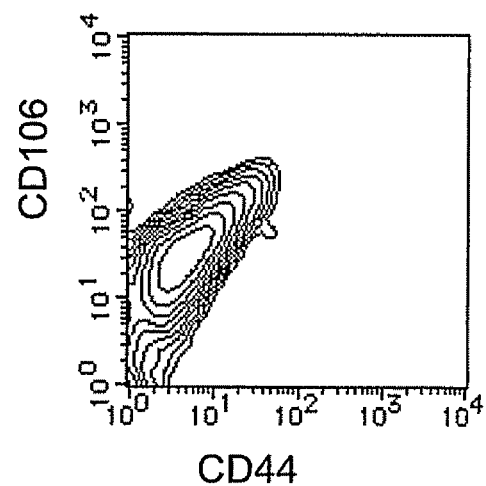
FIG. 7A shows the state of double staining of CD44 and CD106 of EC cells according to Example 6 of the present invention.
Figure 7B:
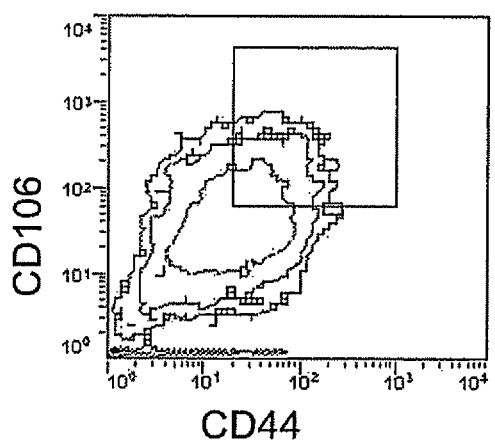
FIG. 7B shows the state of double staining of CD44 and CD106 of the cells at 7 days after RA treatment, according to Example 6 of the present invention.
Figure 7C:
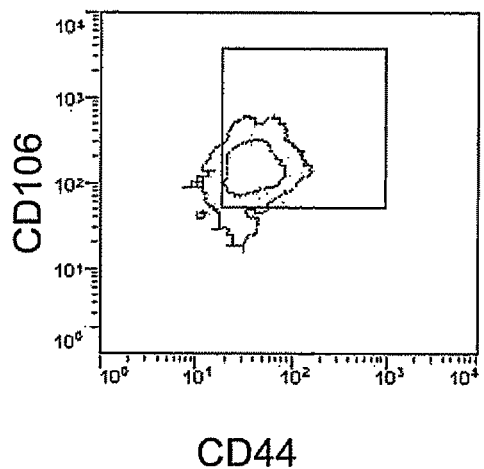
FIG. 7C shows the state of double staining of CD44 and CD106 of the selected CD44-positive and CD106-positive cells according to Example 6 of the present invention.

A cell population obtained by the above treatment, which contains undifferentiated cells, was washed once with HCMF, and 3 mM EDTA-0.5% BSA-PBS(−) was added thereto, followed by incubation thereof at 37° C. After collecting cells, the cells were subjected to double staining with CD44 FITC (BD Pharmingen) and an anti-CD106 antibody (CD106(BD Pharmingen)PE) to separate and obtain a CD44-positive and CD106-positive fraction using Epics ALTRA (Beckman Coulter), and thus a cell population after exclusion of undifferentiated cells, which cell population is composed of only differentiated cells, was obtained. The results are shown in FIG. 7.

(3) Evaluation of Tooth-forming Potential of CD44-Positive and CD106-Positive Cells after RA Treatment Using CD44-positive and CD106-positive cells obtained as above, tooth germ reconstruction and organ culture were carried out in the same manner as in Example 3, for evaluation. After 14 days of organ culture, the cells differentiated into odontoblasts corresponding to a mesenchymal tissue of a tooth, due to the interaction with tooth germ epithelial cells. Further, by the high-density reconstructed tooth germ method, a tooth with a tooth-specific tissue structure, having enamel outside and dentin inside and internal dental pulp cells, was formed Expression of the genes was confirmed with these CD44-positive and CD106-positive DMSO-EC cells in the same manner as in Example 2(2). As a result, they were revealed to be Oct3/4-negative, Nanog-negative, Slug-positive, Pax3-positive and Wnt1-positive as in the case of the CD44-positive and CD29-positive DMSO-EC cells.

Further, when expression of amelogenin, DSPP and periostin were confirmed in the same manner as in Example 4(2), expression of respective mRNAs were observed as in the case of DMSO-EC. Thus, formation of a periodontal tissue having a hard tissue and periodontal membrane was suggested.

Example 7

In the same manner as in Example 6(2) and (3), double staining was carried out on DMSO-EC cells using CD44 FITC and CD106 PE, and existence of CD44-positive and CD106-positive cells were shown. Expression of the genes in these CD44-positive and CD106-positive cells were confirmed in the same manner as in Example 2, and those cells were revealed to be Oct3/4-negative, Nanog-negative, Slug-positive, Pax3-positive and Wnt1-positive as in the case of CD44-positive and CD29-positive DMSO-EC cells.

Using the thus obtained cell population of CD44-positive and CD106-positive cells, a tooth germ reconstruction, organ culture and mRNA expression were carried out in the same manner as in Example 3 and Example 4(2), for evaluation. As a result, a tooth having a specific tissue structure due to the interaction with tooth germ epithelial cells was formed. Further, expression of amelogenin, DSPP and periostin were observed as in the case of Example 4(2). Thus, formation of a periodontal tissue having a hard tissue and periodontal membrane was suggested to be possible.

Thus, differentiation of CD44-positive and CD29-positive cells or CD44-positive and CD106-positive cells could be induced from totipotent stem cells, and, by culturing these cells together with epithelial cells under compartmentalization, a tooth germ could be reconstructed to provide a tooth with a specific structure having enamel and dentin.

Therefore, according to the present invention, mesenchymal cells for the formation of a tooth can be obtained from totipotent stem cells, and a large amount of teeth can be efficiently produced.

The disclosure of Japanese Patent Application No. 2007-011805 is hereby incorporated by reference in its entirety. All the literatures, patent applications and technical standards described in the present specification are hereby incorporated by reference to the same extent as in cases where each literature, patent application or technical standard is concretely and individually described to be incorporated by reference.

The invention claimed is:

1. A method for producing a tooth comprising:
culturing mouse or human pluripotent stem cells in the presence of a differentiation inducer to produce a cell population after differentiation induction treatment, said cell population containing CD44-positive and CD29-positive cells and/or CD44-positive and CD106-positive cells;
selecting, from said cell population after the differentiation induction treatment, the CD44-positive and CD29-positive cells and/or the CD44-positive and CD106-positive cells as mesenchymal cells for the formation of the tooth, or obtaining the CD44-positive and CD29-positive cells and/or the CD44-positive and CD106-positive cells cultured from mouse or human pluripotent stem cells in the presence of a differentiation inducer;
positioning, in a support carrier, a first cell mass consisting essentially of only either one of the mesenchymal cells or epithelial cells derived from a tooth germ and a second cell mass consisting essentially of only the other one of the mesenchymal cells or the epithelial cells derived from a tooth germ, said first and second cell masses being not mixed with each other but made to closely contact with each other; and
culturing said first and second cell masses in said support carrier.

2. The method according to claim 1, wherein said culturing is continued until a periodontal tissue is formed.

3. The method according to claim 1, wherein the differentiation inducer is selected from the group consisting of neural crest cell-inducing factors, neural crest cell development-responsible factors and neural crest cell growth-promoting factors.

4. The method according to claim 1, wherein the method for obtaining mesenchymal cells further comprises removing undifferentiated pluripotent stem cells from the cell population after the differentiation induction treatment.

* * * * *